US006455286B1

(12) United States Patent
Wollowitz et al.

(10) Patent No.: US 6,455,286 B1
(45) Date of Patent: Sep. 24, 2002

(54) PSORALENS FOR PATHOGEN INACTIVATION

(75) Inventors: Susan Wollowitz, Walnut Creek; Aileen Nerio, Fremont, both of CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 09/500,680

(22) Filed: Feb. 9, 2000

Related U.S. Application Data

(63) Continuation of application No. 09/196,935, filed on Nov. 20, 1998, now Pat. No. 6,133,460.
(60) Provisional application No. 60/066,224, filed on Nov. 20, 1997.

(51) Int. Cl.[7] .............................................. C12N 13/00
(52) U.S. Cl. ............................... 435/173.3; 435/173.1; 435/173.7
(58) Field of Search ........................ 435/173.7, 173.3, 435/173.1

(56) References Cited

U.S. PATENT DOCUMENTS

| | | | |
|---|---|---|---|
| 4,124,598 A | 11/1978 | Hearst et al. | |
| 4,169,204 A | 9/1979 | Hearst et al. | |
| 4,196,281 A | * 4/1980 | Hearst et al. | |
| 4,216,154 A | 8/1980 | Kaufman | |
| 4,235,781 A | 11/1980 | Kaufman | |
| 4,269,851 A | 5/1981 | Kaufman | |
| 4,269,852 A | 5/1981 | Kaufman | |
| 4,279,922 A | 7/1981 | Kaufman | |
| 4,294,822 A | 10/1981 | Kaufman | |
| 4,294,847 A | 10/1981 | Kaufman | |
| 4,298,614 A | 11/1981 | Kaufman | |
| 4,321,919 A | 3/1982 | Edelson | |
| 4,328,239 A | 5/1982 | Kaufman | |
| 4,370,344 A | 1/1983 | Kaufman | |
| 4,545,987 A | 10/1985 | Giles et al. | |
| 4,599,303 A | 7/1986 | Yabusaki et al. | |
| 4,613,322 A | 9/1986 | Edelson | |
| 4,617,261 A | 10/1986 | Sheldon | |
| 4,684,521 A | 8/1987 | Edelson | |
| 4,693,981 A | 9/1987 | Wiesehahn | |
| 4,727,027 A | 2/1988 | Wiesehahn | |
| 4,737,454 A | 4/1988 | Dattagupta et al. | |
| 4,748,120 A | * 5/1988 | Wiesehahn | |
| 4,878,891 A | 11/1989 | Judy | |
| 4,960,408 A | 10/1990 | Klainer | |
| 5,030,200 A | 7/1991 | Judy | |
| 5,106,619 A | 4/1992 | Wiesehahn | |
| 5,120,649 A | 6/1992 | Horowitz | |
| 5,176,921 A | * 1/1993 | Wiesehahn et al. | |
| 5,288,605 A | 2/1994 | Lin | |
| 5,354,774 A | 10/1994 | Deckelbaum | |
| 5,418,130 A | 5/1995 | Platz | |
| 5,440,052 A | 8/1995 | Makriyannis et al. | |
| 5,473,083 A | 12/1995 | Heindel | |
| 5,482,828 A | 1/1996 | Lin | |
| 5,516,629 A | 5/1996 | Park | |
| 5,532,146 A | 7/1996 | Cimino | |
| 5,556,993 A | 9/1996 | Wollowitz | |
| 5,571,666 A | 11/1996 | Floyd | |
| 5,578,736 A | 11/1996 | Wollowitz | |
| 5,593,823 A | 1/1997 | Wollowitz | |
| 5,654,443 A | 8/1997 | Wollowitz | |
| 5,683,661 A | 11/1997 | Hearst | |
| 5,709,991 A | 1/1998 | Lin | |
| 5,827,640 A | 10/1998 | Wiggins | |
| 5,827,741 A | 10/1998 | Beattie | |
| 6,171,777 B1 | * 1/2001 | Cook et al. | |

FOREIGN PATENT DOCUMENTS

| | | |
|---|---|---|
| DE | P3928900.1 A | 8/1989 |
| ES | 549788 | 12/1985 |
| PL | 144435 | 1/1985 |
| WO | WO 88/10272 | 12/1988 |
| WO | WO 91/03933 | 4/1991 |
| WO | WO 92/02641 | 2/1992 |
| WO | WO 95/00631 | 1/1995 |
| WO | WO 98/30327 | 7/1998 |

OTHER PUBLICATIONS

"How Safe Is Our Blood", U.S. News and World Report, 68–78 (1994).

Adams, et al., "The Pechmann Reaction," Organic Reactions vol. VII Chapter 1, Wiley, NY (1953).

Alter et al. "Photochemical Decontamination of Blood Components Containing Hepatitis B and Non–A, Non–B Virus," The Lancet (ii: 1446–1450) (1988).

Alter, H., "A reassessment of the literature on the hepatitis G virus" Transfusion 37:569–572(1997).

Ben–Hur & Horowitz "Advance in photochemical approaches for blood sterilization" Photochem. & Photobio. 62:3 383–388 (1995).

Bender, D. et al., "Psoralen synthesis improvements in furano ring formation application to the synthesis of 4,5'8–trimethylpsoralen," J. Org. Chem. 44:13 2176–2180 (1979).

Bender et al. "Synthesis and Derivitization of 8–Acetylpsoralens. Acetyl migrations during Claisen rearrangement" J. Org. Chem. 48:16 pp. 2709–2719 (1983).

(List continued on next page.)

Primary Examiner—Jon Weber
(74) Attorney, Agent, or Firm—Morrison & Foerster LLP; John W. Tessman

(57) ABSTRACT

Psoralen compound compositions are synthesized which have primary amino substitutions on the 3-, 4-, 5-, and 8-positions of the psoralen, which yet permit their binding to nucleic acid of pathogens. Reaction conditions that photoactivate these psoralens result in the inactivation of pathogens which contain nucleic acid. The compounds show similar activity in test systems to 4' and 5' derivatives of proralen useful for inactivation of pathogens in blood products. In addition to the psoralen compositions, the invention contemplates such inactivating methods using the new psoralens.

6 Claims, No Drawings

OTHER PUBLICATIONS

Bertolini, F., et al., "Platelet Quality After 15–day Storage of Platelet Concentrates Prepared from Buffy Coats and Stored in Glucose–Free Crystalloid Medium," Transfusion 32:9–16 (1992).

Blajchman, M.A., *Blood Safety: Current Challenges,* S.J. Nance ed. "Bacteria in the blood supply: An overlooked issue in transfusion medicine" pp. 213–228 (1992).

Bowden, R.A. *Blood Safety: Current Challenges,* S.J. Nance ed "Cytomegalovirus: Transmission by Blood Components and Measures of Prevention" pp. 201–211 (1992).

Charalambous et al. "5'–Azido–(8–THC: A novel photoaffinity label for the cannabinoid receptor" Med. Chem. 35:3076–3079 (1992).

Chiu, E. et al., "A prospective study of symptomatic bacteremia following platelet transfusion and of its management" Transfusion 34:950–954 (1994).

Cimino et al. "Psoralens as Photoactive Probes of Nucleic Acid Structure and Function: Organic Chemistry, Photochemistry, and Biochemistry," Ann. Rev. Biochem. 54:1151–1193 (1985).

Cotten M. et al., "Psoralen treatment of adenovirus particles eliminates virus replication and transcription while maintaining the endosomolytic activity of the virus capsid," Virology 205: 254–261 (1994).

Crombie, L. et al. "Synthesis of the Mammea Coumarins Part 2. Experiments in the Mammea E series and synthesis of Mammea E/AC" J. Chem. Soc. Perk. Trans. I 333–343 (1987).

Dodd et al. "Inactivation of viruses in platelet suspensions that retain their in vitro characteristics: comparison of psoralen–ultraviolet A and merocyanine 540 visible light methods," Transfusion 31:483–490 (1991).

Dodd, Blood Supply: Risks, Perceptions, and Prospects for the Future S.J. Nance ed. p. 1 (1994).

Dodd, R. Y. "Will blood products be free of infectious agents?" Nance S.J. ed. *Transfusion Med. in the 1990's* AABB (1990).

Elix et al., "Synthetic confirmation of the structure of the lichen benzyl esters alectorialic and barbatolic acids" Aust. J. Chem. 40:1841–50 (1987).

Elsner and Mouritsen "Use of psoralens for covalent immobilization of biomolecules in solid phase assays" Bioconjugate Chem. 5(5):463–467 (1994).

Fall et al. "A convenient synthesis of benzofuran–3–acetic acids" Heterocylces 41:647–650 (1995).

Friedman L and Stromberg R. "Viral inactivation and reduction in cellular blood products," Rev. Fr. Transfus. Hemobiol. 36:83–91 (1993).

Gasparro et al., "Receptor–mediated photo–cytotoxicity: synthesis of photoactivatable psoralen derivative conjugated to insulin" Biochem. and Biophys. Res. Comm. 141(2):502–509 (1986).

Goldenberg et al. "Synthesis and Properties of Novel Psoralen Derivatives," Biochemistry 27:6971–6976 (1988).

Groene S. and Shaw D. :Psoralen preparation of antigenically intact noninfectious rotavirus particles, J. Virol. Methods 38 93–102 (1992).

Gupta et al., "Synthesis of organomagnesium (–diketonates and alkoxides" J. Organomet. Chem 452:1–4 (1993).

Hansen J. et al. "Psoralenamines. 3.[1]Synthesis, pharmacological behavior, and DNA binding of 5–(aminomethyl)–8methoxy–, 5–[[(3–aminopropyl)oxy]methyl]–, and 8–[(3–aminopropyl)oxy]psoralen derivatives" J. Med. Chem. 28:1001–1010 (1985).

Hanson, C.V. "Photochemical Inactivation of Viruses with Psoralens: An Overview," Blood Cells: 18:7–25 (1992).

Hearst et al. "The Reaction of the Psoralens with Deoxyribonucleic Acid," Quart. Rev. Biophys. 17:1–44 (1984).

Hearst, J.E., and Thiry, L., "The photoinactivation of an RNA animal virus, vesicular stomatitis virus, with the aid of newly synthesized psoralen derivatives," Nucleic Acids Research, 4:1339–1347 (1977).

Heinmets, et al., "Inactivation of viruses in plasma by photosensitized oxidation." Walter Reed Research Report WRAIR 53–55. (1955) pp. 1–16.

Hilfenhaus, J., et al., "A strategy for testing established plasma protein manufacturing procedures for their ability to inactivate or eliminate human immunodeficiency virus," J. Biol. Std. 15:251–263 (1987).

Horowitz, B., et al., "Inactivation of viruses in labile blood derivatives," Transfusion 25:516–522 (1985).

Hyde and Hearst, "Binding of Psoralen Derivatives to DNA and Chromatin: Influence of the Ionic Environment on Dark Binding and Photoreactivity," Biochemistry 17:1251–1252 (1978).

Isaacs et al. "A Photochemical Characterization of Reactions of Psoralen Derivatives with DNA," Trends in Photobiology (Plenum) pp. 279–294 (1982).

Isaacs et al. "In Vitro Characterization of the Reaction of Four Psoralen Derivatives with DNA," NCI Monograph 66:21–20 (1984).

Isaacs et al. "Synthesis and Characterization of New Psoralen Derivatives with Superior Photoreactivity with DNA and RNA," Biochemistry 16:1058–1064 (1977).

Kaufman K. et al., "Reactions of furocoumarins II(1). Synthetic aminomethyl psoralens via chloromethylationor benzylic bromination," J. Heterocyclic Chem. 19 1051–1056 (1982).

Lackritz E., et al. "Estimated risk of transmission of HIV by screened blood in the United States," New Eng. J. Med. 333:1721 (1995).

Lambert et al., "Application of the intramolecular aza–wittig reaction to the synthesis of vinylogous urethanes and amides" J. Org. Chem. 50:5352 (1985).

Lee, B.L., et al., "Interaction of Psoralen–Derivatized Oligodeoxyrionucleoside Methylphosphonates with Single–Stranded DNA," Biochemistry, 27:3197–3203 (1988).

Lin et al. "Photochemical inactivation of viruses and bacteria inplatelet concentrates by use of a novel psoralen and long–wavelength ultraviolet light", Transfusion 37:423–435 (1997).

Lin et al. "Use of 8–Methoxypsoralen and Long–Wavelength Ultraviolet Radiation for Decontamination of Platelet Concentrates," Blood 74:517–525 (1989).

MacLeod and Worth "Synthesis of benzofuranoid systems. I. Furocoumarins, benzofurans and dibenzofurans," Tetrahedron Letters No. 3, pp. 237–240 Pergamon Press (1972).

March, J. "Reactions, mechanisms, and structure," Advanced Organic Chemistry 34d Ed. Wiley (1985).

Margolis–Nunno et al. "Photochemical Virus Sterilization in Platelet Concentrates with Psoralen Derivatives," Thromb. Haemostas. 65:1162 (Abstract) (1991).

Margolis–Nunno et al. "Virus sterilization in platelet concentrates with psoralen and ultraviolet A light in the presence of quencers" Transfusion 32:6 541–547 (1992).

Matthews, J.L., et al., "Photodynamic therapy of viral comtaminants with potential for blood banking applications," Transfusion 28:81–83 (1988).

Morel et al. "Photochemical Inactivation of Viruses and Bacteriophage in Plasma and Plasma Fractions," Blood Cells 18:27–42 (1992).

Moroff et al. "Factors influencing virus inactivation and retention of platelet properties following treatment with aminomethyltrimethylpsoralen and ultraviolet A light" Blood Cells 18:43–56 (1992).

Moroff, G. et al., "The influence of irradiation on stored platelets," Transfusion 26:453–456 (1986).

Morrow et al. "Septic Reactions to Platelet Transfusions," JAMA 266:555–558 (1991).

Olah and Kuhn, "Selective Friedel Crafts Reactions. I. Boron haldie catalyzed haloalkylation of benzene and alkylbenzenes with fluorohaloalkanes," J. Org. Chem., 29, 2317 (1964).

Olah, ed., "Friedel–Crafts and Related Reactions, vol. II, Part 2 Alkylation and related reactions," Interscience, NY, (1964) p. 749.

Prince, A.M., et al., "β–Propiolactone/Ultraviolet Irradiation: A review of Its Effectiveness for Inactivation of Viruses in Blood Derivatives," Reviews of Infect. Diseases 5:92–107 (1983).

Proudouz, K.N., et al., "Use of Laser U–V for Inactivation of Virus in Blood Platelets," Blood 70:589–592 (1987).

Rai, S. et al., "Dramatic Improvements in Viral Inactivation with Brominated Psoralens, Naphthalenes and Anthracenes" *Photochem. and Photobio.* (1993) 58:59–65.

Rao, K. E., "Psoralen–lexitropsin hybrids: DNA sequence selectivity of photoinduced cross–linking from MPE footprinting and exonuclease III stop assay, and mode of binding from electric linear dichroism," Anti–cancer Drug Design 9:221–237 (1994).

Seebach et al. "Synthesis of chiral starburst dendrimers from PHB–derived triols as central cores," Helv. Chim. Acta 77:1673 (1994).

Tessman et al. "Photochemistry of the Furan–Side 8–Methoxypsoralen–Thymide Monoadduct Inside the DNA Helix. conversion to Diadduct and to Pryone–Side Monoadduct," Biochem. 24:1669–1676 (1985).

Wagner et al. "Determination of residual 4'–aminomethyl–4, 5',8–trimethylpsoralen and mutagenicity testing following psorlen plus UVA treatment of platelet suspensions" Photochem. & Photobio. 57:5 819–824 (1993).

Wagner, et al. "Approaches to the reduction of viral infectivity in cellular blood components and single donor plasma" Trans. Med. Rev. V:1 18–32 (1991).

Wagner, S. et al. Photochem. Photobio. Meeting Abstract 113s (1992).

Wang Z. et al, "Chemical conversion of a trans–activation responsive RNA–binding fragment of HIV–1 tat protein into site–specific cross–linking agent," J. Am. Chem. Soc. 117(20):5438–5444 (1995).

* cited by examiner

PSORALENS FOR PATHOGEN INACTIVATION

REFERENCE TO RELATED APPLICATIONS

This application is a continuation of application Ser. No. 09/196,935 filed on Nov. 20, 1998, now U.S. Pat. No. 6,133,460, which claims priority to U.S. Provisional Patent Application Ser. No. 60/066,224, filed Nov. 20, 1997; the disclosure of which is hereby incorporated by reference.

STATEMENT OF RIGHTS TO INVENTIONS MADE UNDER FEDERALLY SPONSORED RESEARCH

This invention was made with United States government support under SBIR Grant No. 1 R43 HL51796-01 from the NIH. The United States Government has certain rights in this invention.

FIELD OF THE INVENTION

The present invention provides new psoralens having enhanced ability to inactivate pathogens in the presence of ultraviolet light. The present invention also provides methods of using new psoralens to inactivate pathogens in health related products to be used in vivo and in vitro, and in particular, blood products.

BACKGROUND

Psoralens are tricyclic compounds formed by the linear fusion of a furan ring with a coumarin. Psoralens can intercalate between the base pairs of double-stranded nucleic acids (or base paired regions of single-stranded nucleic acids), forming covalent adducts to pyrimidine bases upon absorption of long wave ultraviolet light (UVA). G. D. Cimino et al., Ann. Rev. Biochem. 54:1151 (1985); Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink [S. T. Isaacs et al., Biochemistry 16:1058 (1977); S. T. Isaacs et al., Trends in Photobiology (Plenum) pp. 279–294 (1982); J. Tessman et al., Biochem. 24:1669 (1985); Hearst et al., U.S. Pat. Nos. 4,124,598, 4,169,204, and 4,196,281, hereby incorporated by reference].

The photoreaction of psoralens with nucleic acid has been useful in the study of nucleic acid folding, the attachment of diagnostic probes tolnucleic acids, the attachment of nucleic acids to surfaces and materials, the blocking of polymerase reactions and the inactivation of organisms and cells that require nucleic acid replication to proliferate, e.g., bacteria, viruses, leukocytes and overproliferating cells, such as those resulting in psoriasis, restenosis, or cancer. The inactivation of a virus can also be applied to preparation of vaccines. The level of reaction with cellular nucleic acid can be modulated to stop proliferation of the cell yet maintain cell functions such as protein synthesis. This can be applied to the treatment of T-cell lymphocytes as a means of preventing graft vs. host disease in, for example, bone marrow transplants.

The use of psoralens for pathogen inactivation in blood products is of particular interest as the safety of the blood supply is an issue of universal concern. While transfusion associated viral infections have been considerably reduced by testing, transmission of human immunodeficiency virus (HIV), hepatitis B virus (HBV) and hepatitis C virus (HCV) continue to occur in $1/450,000$ to 660,000 units, $1/200,000$) units and $1/3000$ units respectively [R. Dodd, Blood Supply: Risks, Perceptions, and Prospects for the Future, S. J. Nance, ed., p.1 (1994); E. Lackritz et al., New Eng. J. Med. 333: 1721 (1995)]. Testing is not an option for some viruses. Cytomegalovirus is commonly found within the blood supply yet is of clinical importance only to immune compromised patients for which infection can be fatal [R. Bowden, Blood Safety: Current Challenges, S. J. Nance, ed., p.201 (1992)]. Universal screening for CMV would lead to a serious reduction in eligible donors and thus a reduction in the national blood supply. Special donor pools must be used for these patients at present. It is also recognized that other unknown viruses or new strains of known viruses may find their way into the blood supply and will not be identified until morbidity or mortality is noted, nor will they be able to be screened out until tests become available. The identification of hepatitis G in blood units is the most recent example of such an occurrence [H. Alter, Transfusion 37: 569 (1997)].

Bacterial contamination, especially of platelet concentrates (PC) has been increasingly recognized as a problem as well. It is estimated that $1/1,000$ to 2,000 PC units show levels of contamination that results in a septic response [J. Morrow et al., JAMA 266: 555 (1991); M. Blajchman, Blood Safety: Current Challenges, S. J. Nance, ed., p.213 (1992); E. Chiu et al., Transfusion 34: 950 (1994)]. There are at present no screening tests available for blood units for any of the ten or so bacteria that have been associated with fatal transfusion associated sepsis in the United States. While there are potential methods for storage of platelets at lower temperatures to alleviate this problem [U.S. Pat. Nos. 5,827,640 and 5,827,741], inactivation of the bacteria by psoralen would have far less impact on the routine storage of platelets.

Psoralens are ideal candidates for photosensitized, decontamination of platelet concentrates [H. Alter et al., Lancet ii:1446 (1988); L. Lin et al., Blood 74: 517 (1989); C. Hanson, Blood Cells 18: 7 (1992)]. For example, 8-methoxypsoralen (8-MOP) is quite effective at deactivation of a number of bacteria found in platelet concentrates. However, it is not sufficiently active to inactive pathogens with small genomes (i.e., viruses) without using concentrations and irradiation times which damage platelets. The highly active psoralen, 4'-aminomethyl-4,5',8-trimethylpsoralen (AMT), exhibits excellent photochemical inactivation properties but is highly mutagenic in the absence of light in some bacterial assays [S. Wagner et al., Photochem. Photobio. Meeting Abstract, 55: 113S (1992)]. Other 4'- and 5'-aminomethyl substituted psoralens have been developed which show excellent photochemical inactivation properties with considerable reduction in mutagenicity.

Several patents are directed toward psoralen inactivation of pathogens in blood products [G. Wiesehahn et al., U.S. Pat. Nos. 4,727,027 and 4,748,120, L. Lin et al., U.S. Pat. Nos. 5,288,605, 5,482,828, and 5,709,991, and S. Wollowitz et al., U.S. Pat. No. 5,593,823, hereby incorporated by reference]. P. Morel et al., Blood Cells 18:27 (1992) show that 300 μg/mL of 8-MOP together with ten hours of irradiation with ultraviolet light can effectively inactivate viruses in human serum. Similar studies using 8-MOP and AMT have been reported by other investigators [Dodd R Y, et al., Transfusion 31:483–490 (1991); Margolis-Nunno, H., et al., Thromb Haemostas 65: 1162 (Abstract)(1991)]. Indeed, the photoinactivation of a broad spectrum of microorganisms has been established, including HBV, HCV, and IV. [Hanson C. V., Blood Cells: 18: 7–24 (1992); Alter, H. J., et al., The Lancet ii:1446 (1988); Margolis-Nunno H. et al., Thromb Haemostas 65: 1162 (Abstract) (1991); Lin et al. Transfusion 37: 423 (1997)]. There are clearly a broad class of psoralen compounds effective in the inactivation of pathogens in general and particularly in blood products.

The most highly active psoralen compounds useful for inactivation have amino derivatives on the 4' and 5' positions [Wollowitz et al., U.S. Pat. Nos. 5,578,736 and 5,654,443, Kaufman U.S. Pat. No. 4,294,822]. 5-alkoxy and 8-alkoxypsoralens with amino substituents at the 8 or 5 position, respectively, as well as 8-aminomethyl psoralen and 8-aminomethyl-4-methylpsoralen are known [J. Hansen et al., J. Med. Chem. 28: 1001–1010 (1985); Kaufman U.S. Pat. Nos. 4,269,851 and 4,328,239]. The limited data provided for these latter compounds suggested that even the amino substituted alkoxypsoralens have relatively poor photoactivity and that amino substitution at the furan ring is important for high photoactivity. Also, these compounds are formed by methods which offer little flexibility in modifying the ring functionality.

SUMMARY OF THE INVENTION

The present invention provides new aminopsoralens with unpredicted photoreactivity with nucleic acids that can be used for nucleic acid probe preparations, preparation of conjugates, inhibition of cell proliferation, inactivation of virus for vaccine preparation, and in particular, for the inactivation of pathogens in blood products. The present invention also provides new routes to the synthesis of aminopsoralens and intermediates that may be useful for providing psoralens conjugated to a variety of other functional groups.

With respect to new compounds, some of the new psoralens are primaryamino-pyrone-linked psoralens comprising a primaryamino group (i.e. —$NH_2$ group) linked to the pyrone ring of the psoralen (3- and 4-carbon atoms) via an alkyl chain optionally containing oxygen and nitrogen atoms, and wherein the psoralen ring may have one or more alkyl groups at other positions. The present invention further contemplates psoralen compounds with a primaryamino substituent on the pyrone ring, comprising: a) a substituent A on the pyrone ring, selected from the group consisting of: —$(CH_2)_u$—$NH_2$, —$(CH_2)_w$—J—$(CH_2)_z$—$NH_2$, —$(CH_2)_w$—J—$(CH_2)_x$—K—$(CH_2)_z$—$NH_2$, and —$(CH_2)_w$—J—$(CH_2)_x$—K—$(CH_2)_y$—L—$(CH_2)_z$—$NH_2$; wherein J, K, and L are independently selected from the group consisting of O and NH, in which u is a whole number from 1 to 10, w is a whole number from 1 to 5, x is a whole i: number from 2 to 5, y is a whole number from 2 to 5, and z is a whole number from 2 to 6; and b) substituents B, $R_3$, $R_4$, $R_5$, and $R_6$ on the pyrone ring (the 3- or 4-carbon atom which does not have the primaryamino substituent), 5-, 4'-, 5'- and 8-carbon atoms respectively, independently selected from the group consisting of —H and —$(CH_2)_v CH_3$, where v is a whole number from 0 to 5; or a salt thereof. Where an element is "independently selected" from a group, it means that the element need not be the same as other elements chosen from the same group. The structure of these compounds is as follows.

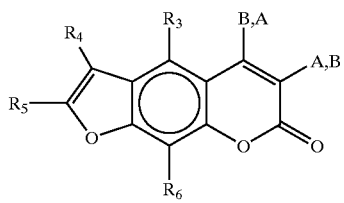

I

The present invention further contemplates compounds of the above structure with a primaryamino substituent on the pyrone ring, wherein A is at the 3-carbon atom and B is at the 4-carbon atom, preferably wherein A is selected from the group consisting of —$CH_2$—$NH_2$ and —$CH_2$—O—$(CH_2)_2$—$NH_2$. More specifically, the invention contemplates compounds wherein A is —$CH_2$—$NH_2$, and wherein B, $R_3$, $R_5$, and $R_6$ are —H, and wherein $R_4$ is —$CH_3$; wherein A is —$CH_2$—$NH_2$, and wherein $R_3$ and $R_5$ are —H, and wherein B, $R_4$, and $R_6$ are —$CH_3$; wherein A is —$CH_2$—$NH_2$, and wherein $R_3$ and $R_4$ are —H, and wherein B, $R_5$, and $R_6$ are —$CH_3$; wherein A is —$CH_2$—$NH_2$, and wherein $R_3$ is —H, and wherein B, $R_4$, $R_5$, and $R_6$ are —$CH_3$; wherein A is —$CH_2$—O—$(CH_2)_2$—$NH_2$, and wherein $R_3$ and $R_5$ are —H, and wherein B, $R_4$, and $R_6$ are —$CH_3$. The structure of these compounds is as follows.

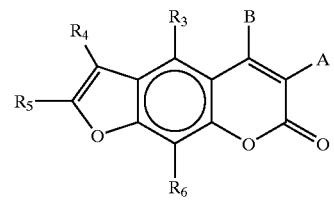

II

The present invention further contemplates compounds of the above structure with a primaryamino substituent on the pyrone ring, wherein A is at the 4-carbon atom and B is at the 3-carbon atom, preferably wherein A is selected from the group consisting of —$CH_2$—$NH_2$ and —$CH_2$—O—$(CH_2)_2$—$NH_2$. More specifically, the invention contemplates compounds wherein A is —$CH_2$—$NH_2$, and wherein B, $R_3$, $R_5$, and $R_6$ are —H, and wherein $R_4$ is —$CH_3$; wherein A is —$CH_2$—$NH_2$, and wherein B and $R_3$ are —H, and wherein $R_4$, $R_5$, and $R_6$ are —$CH_3$; wherein A is —$CH_2$—O—$(CH_2)_2$ —$NH_2$, and wherein B and $R_3$ are —H, and wherein $R_4$, $R_5$, and $R_6$ are —$CH_3$. The structure of these compounds is as follows.

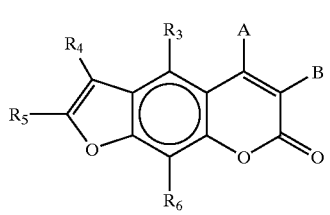

III

Additionally some of the new psoralens are primaryamino-benzene-linked psoralens comprising a primaryamino group linked to the benzene ring of the psoralen (5- and 8-carbon atoms) via an alkyl chain optionally containing oxygen and nitrogen atoms, and wherein the psoralen ring may have one or more alkyl, groups at other positions. The present invention further contemplates psoralen compounds with a primaryamino substituent on the benzene ring, comprising: a) a substituent A on the benzene ring, selected from the group consisting of: $-(CH_2)_u-NH_2$, $-(CH_2)_w-J-(CH_2)_z-NH_2$, $-(CH_2)_w-J-(CH_2)_x-K-(CH_2)_z-NH_2$, and $-(CH_2)_w-J-(CH_2)_x-K-(CH_2)_y-L-(CH_2)_z-NH_2$; wherein J, K, and L are independently selected from the group consisting of O and NH, in which u is 1 whole number from 1 to 10, w is a whole number from 1 to 5, x is a whole number from 2 to 5, y is a whole number from 2 to 5, and z is a whole number from 2 to 6; and b) substituents B, $R_1$, $R_2$, $R_4$, and $R_5$ on the benzene ring (the 5- or 8-carbon atom which does not have the primaryamino substituent), 3-, 4-, 4'-, and 5'-carbon atoms respectively, independently selected from the group consisting of —H and $-(CH_2)_v CH_3$, where v is a whole number from 0 to 5, or a salt thereof; except c) when A is $-CH_2-NH_2$ and at the 8-carbon atom, one of B, $R_1$, $R_4$, and $R_5$ must be $-(CH_2)_v CH_3$. Where an element is "independently selected", from a group, it means that the element need not be the same as other elements chosen from the same group. The structure of these compounds is as follows.

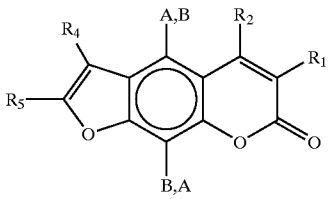

IV

The present invention further contemplates compounds of the above structure with a primaryamino substituent on the benzene ring, wherein A is at the 5-carbon atom and B is at the 8-carbon atom, preferably wherein A is selected from the group consisting of $-CH_2-NH_2$ and $-CH_2-O-(CH_2)_2-NH_2$. More specifically, the invention contemplates compounds wherein A is $-CH_2-NH_2$, and wherein B, $R_1$, $R_2$, $R_4$, and $R_5$ are —H; wherein A is $-CH_2-O-(CH_2)_2-NH_2$, and wherein B, $R_1$, and $R_2$ are —H, and wherein $R_4$ and $R_5$ are $-CH_3$. The structure of these compounds is as follows.

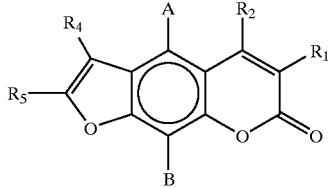

V

The present invention further contemplates compounds of the above structure with a primaryamino substituent on the benzene ring, wherein A is at the 8-carbon atom and B is at the 5-carbon atom, preferably wherein A is selected from the group consisting of $-CH_2-NH_2$ and $CH_2-O-(CH_2)_2-NH_2$, and wherein when A is $-CH_2-NH_2$, at least one of B, $R_1$, $R_4$, and $R_5$ are $-(CH_2)_v CH_3$. More specifically, the invention contemplates compounds wherein A is $-CH_2-NH_2$, and wherein B, $R_1$, and $R_4$ are —H, and wherein $R_2$ and $R_5$ are $-CH_3$; wherein A is $-CH_2-NH_2$, and wherein B and $R_1$ are —H, and wherein $R_2$, $R_4$, and $R_5$ are $-CH_3$; wherein A is $-CH_2-O-(CH_2)_2-NH_2$, and wherein B and $R_1$ are —H, and wherein $R_2$, $R_4$, and $R_5$ are $-CH_3$. The structure of these compounds is as follows.

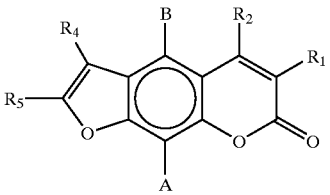

VI

The present invention also provides new routes to the synthesis of amninopsoralens and intermediates that may be useful for providing psoralens conjugated to a variety of other functional groups.

Without intending to be limited to any method of synthesis, the compounds of the present invention can be prepared by introduction of the amino functionality (or of a building block for said primaryamino group) in a protected form early on in the synthesis before the psoralen ring is fully constructed. This method provides new routes to the synthesis of primaryamino-pyrone-linked and benzene-linked psoralen s that allow more flexibility in the ring substituents than existing methods. This is exemplified in the synthesis of 3-aminomethyl-4'-methylpsoralen, 3-aminomethyl-4,4',8-trimethylpsoralen, 3-aminomethyl-4,5',8-trimethylpsoralen, 3-aminomethyl-4,4',5',8-tetramethylpsoralen, 3-(4-amino-2-oxa)butyl-4, 4',8 trimethylpsoralen, 4-aminomethyl-4'-methylpsoralen, 4-aminomethyl(4',5',8-trimethylpsoralen, 4-(4-amino-2-oxa)butyl-4',5',8-trimethylpsoralen, 5-aminomethylpsoralen, 5-(4-amino-2-oxa)butyl-4', 5'dimethylpsoralen, 8-aminomethyl-4,4',5-trimethylpsoralen aminomethyl4,5'-dimethylpsoralen), and 8-(4-amino-2-oxa)butyl-4,4',5'-trimethylpsoralen (described in the examples below).

The present invention contemplates methods of inactivating pathogens in a biological composition, comprising, in the following order: a) providing, in any order, i) a compound selected from the group consisting of primaryamino-pyrone-linked psoralens and primaryamino-benzene-linked psoralens; ii) photoactivating means for photoactivating said compounds; and iii) a biological composition suspected of being contaminated with a pathogen which contains nucleic acid; b) adding said compound to said biological composition; and c) photoactivating said compound, so as to inactivate said pathogen. In one embodiment, the biological composition is a blood product. In a preferred embodiment, the blood product is either platelets or plasma. A preferred method of the present invention is performed in a blood bank or similar setting, wherein said compound is formulated in solution and said solution is contained in a blood compatible bag, and wherein said compound is added to said biological composition by flowing said biological composition through said bag. After treatment with the method, the blood product is suitable for its intended use.

A biological composition is defined as a composition originating from a biological organism of any type. Examples of biological compositions include, but are not limited to, blood, blood products (such as plasma, platelet preparations, red blood cells, packed red blood cells, and serum), cerebrospinal fluid, saliva, urine, feces, semen, sweat, milk, tissue, tissue samples, homogenized tissue samples, and any other substance having its origin in a biological organism. Biological compositions also include synthetic material incorporating a substance having its origin in a biological organism, such as a vaccine preparation comprised of alum and a pathogen (the pathogen being the substance having its, origin in a biological organism), cell culture medium, cell cultures, viral cultures, and other cultures derived from a biological organism.

A pathogen is defined as any agent which contains nucleic acid and is capable of causing disease in a human, other mammals, or vertebrates. Examples include microorganisms such as unicellular or multicellular microorganisms including but not limited to bacteria, viruses, protozoa, fungi, yeasts, molds, and mycoplasmas. The pathogen can comprise either DNA or RNA and this nucleic acid can be single stranded or double stranded.

The present invention contemplates that the photoactivating means comprises a photoactivation device capable of emitting a given intensity of a spectrum of electromagnetic radiation comprising wavelengths between 180 nm and 400 nm, preferably between 300 nm and 400 nm, and in particular, between 320 nm and 380 nm. It is preferred that the intensity is between 1 and 30 mW/cm$^2$ and that the mixture is exposed to this intensity for between one second and thirty minutes [U.S. Pat. No. 5,593,823].

The present invention contemplates embodiments wherein said blood preparation is in a synthetic media. In one embodiment, the concentration of compound is between 0.1 $\mu$M and 1000 $\mu$M, preferably between 1 $\mu$M and 500 $\mu$M. In a preferred embodiment, the compound is added to said blood preparation at a concentration of between 10 $\mu$M and 250 $\mu$M.

The present invention contemplates embodiments of the methods where inactivation is performed without limiting (e.g. reducing) the concentration of molecular oxygen. Preferably, inactivation is performed without limiting the concentration of singlet oxygen that may be formed during the photoreaction step. Furthermore, there is no need for the use of cosolvents (e.g. dimethyl sulphoxide (DMSO)) to increase compound solubility.

In one embodiment, the present invention Contemplates methods of inactivating microorganisms in a blood product, wherein the compound is a primaryamino-pyrone-linked psoralen, comprising: a) a substituent A on the pyrone ring, selected from the group consisting of: —(CH$_2$)$_u$—NH$_2$, —(CH$_2$)$_w$—J—(CH$_2$)$_z$—NH$_2$, —(CH$_2$)$_w$—J—(CH$_2$)$_x$—K—(CH$_2$)$_z$—NH$_2$, and —(CH$_2$)$_w$—J—(CH$_2$)$_x$—K—(CH$_2$)$_y$—L—(CH$_2$)$_z$—NH$_2$; wherein J, K, and L are independently selected from the group consisting of O and NH, in which u is a whole number from 1 to 10, w is a whole number from 1 to 5, x is a whole number from 2 to 5, y is a whole number from 2 to 5, and z is a whole number from 2 to 6; and b)substituents B, R$_3$, R$_4$, R$_5$, and R$_6$ on the pyrone ring, 5-, 4'-, 5'- and 8-carbon atoms respectively, independently selected from the group consisting of —H and —(CH$_2$)$_v$CH$_3$, where v is a whole number from 0 to 5; or a salt thereof.

Alternatively, the present invention contemplates embodiments of the method of inactivation, wherein the compound is a primaryamino-benzene-linked psoralen comprising: a) a substituent A on the benzene ring, selected from the group consisting of: —(CH$_2$)$_u$—NH$_2$, —(CH$_2$)$_w$—J—(CH$_2$)$_z$—NH$_2$, —(CH$_2$)$_w$—J—(CH$_2$)$_x$—K—(CH$_2$)$_z$—NH$_2$, and —(CH$_2$)$_w$—J—(CH$_2$)$_x$—K—(CH$_2$)$_y$—L—(CH$_2$)$_z$—NH$_2$; wherein J, K, and L are independently selected from the group consisting of O and NH, in which u is a whole number from 1 to 10, w is a whole number from 1 to 5, x is a whole number from 2 to 5, y is a whole number from 2 to 5, and z is a whole number from 2 to 6; and b) substituents B, R$_1$, R$_2$, R$_{44}$ and R$_5$ on the benzene ring, 3-, 4-, 4'-, and 5'-carbon atoms respectively, independently selected from the group consisting of —H and —(CH$_2$)$_v$CH$_3$, where v is a whole number from 0 to 5; or a salt thereof, except c) when A is —CH$_2$—NH$_2$ and at the 8-carbon atom, one of B, R$_1$, R$_4$, and R$_5$ must be —(CH$_2$)$_v$CH$_3$.

In one embodiment of the method of inactivation, at least two of the compounds are present. The present invention contemplates embodiments where the compound is introduced either in aqueous solutions, such as water, saline, or a synthetic media, preferably a phosphate buffered media, non aqueous solutions such as alcohols, polyethylene glycols, or solvent mixtures with water, or in a dry formulation in which additives may be present. In one embodiment, the present invention contemplates a synthetic platelet storage media, comprising a glucose and magnesium free aqueous solution of: 45–120 mM sodium chloride; 5–15 mM sodium citrate; 20–40 mM sodium acetate; and 20–30 mM sodium phosphate. In a preferred embodiment, the aqueous solution comprises: approximately 86 mM sodium chloride; approximately 10 mM sodium citrate; approximately 30 mM sodium acetate; and approximately 26 mM sodium phosphate. The solution has a pH of approximately 300 milliosmolar/Kg. By not containing glucose or magnesium, the media is readily autoclaved.

The present invention contemplates embodiments wherein the compound may be introduced to the reaction vessel at the point of manufacture. Alternatively, the compound may be added to the reaction vessel at some point after the manufacture of, for example, a blood product. In one embodiment, a solution of the psoralen is provided in a biocompatible container that is attached to a disposable plastic set containing a unit of platelets or plasma. The psoralen solution is mixed with the blood product by passing said blood product through the container of psoralen and the resultant mixture is photoactivated with an illumination device suitable for uniform irradiation of blood bags [U.S. Pat. No. 5,593,823]. In a further embodiment, the residual psoralen and any low molecular weight psoralen photoproducts are removed from the solution [PCT publication WO 98/30327, hereby incorporated by reference].

In one embodiment, the blood product is admixed with the psoralen and the mixture is passed through a flow system where it is passed over a static light source resulting in photoactivation of said psoralen. The means of passing through said flow system includes but is not limited to gravity flow or metered flow, using a pump system.

DESCRIPTION OF THE INVENTION

The present invention provides new psoralens and methods of synthesis of new psoralens having enhanced ability to inactivate pathogens in the presence of ultraviolet light. The new psoralens are potentially effective against a wide variety of pathogens. The present invention also provides methods of using new and known compounds to inactivate pathogens in biological products to be used if vivo and in vitro, and in particular, blood products.

The inactivation methods of the present invention provide ex vivo methods of inactivating pathogens, and in particular, viruses, in blood products prior to use in vitro or in vivo. In contrast with previous approaches, the method requires only short irradiation times and there is no need to limit (e.g. reduce) the concentration of molecular oxygen or of singlet oxygen present or generated in the system.

In vivo use of a material is defined as introduction of the material or compound into a living human, mammal, or vertebrate. In vitro use of material or compound is defined as a use of the material or compound outside a living human, mammal, or vertebrate, where neither the material nor compound is intended for reintroduction into a living human, mammal, or vertebrate. An example of an in vitro use would be the analysis of a component of a blood sample using laboratory equipment. Ex vivo use of a compound is defined as using a compound for treatment of a biological material such as a blood product outside of a living human, mammal, or vertebrate, where that treated biological material is intended for use inside a living human, mammal, or vertebrate. For example, removal of blood from a human and introduction of a compound into that blood to inactivate pathogens is defined as an ex vivo use of that compound if the blood is intended for reintroduction into that human or another human. Reintroduction of the human blood into that human or another human would be in vivo use of the blood, as opposed to the ex vivo use of the compound.

The description of the invention is divided into the following sections: I) Compound Synthesis, II) Photoactivation Devices, III) Binding of Compounds to Nucleic Acid, IV) Inactivation of Nucleic Acid Containing Materials V) Preservation of Biochemical Properties of Material Treated, VI) Psoralen Conjugates and Other uses of Psoralens.

I. Compound Synthesis

A. Psoralens as Photoactivation Compounds

The present invention contemplates those compounds described as psoralens: [7H -furo(3,2-g)-(1)-benzopyran-7-one, or b-lactone of 6-hydroxy-5-benzofuranacrylic acid], which are linear:

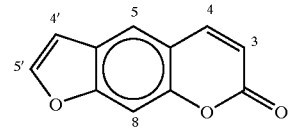

and in which the two oxygen residues appended to the central aromatic moiety have a 1, 3 orientation, and further in which the furan ring moiety is linked to the 6-position of the two ring coumarin system. Psoralen derivatives are derived from substitution of the linear furocoumarin at the 3-, 4-, 5-, 8-, 4'-, or 5'-carbon atoms indicated in the above structure. For the purpose of this invention, substituents on the psoralen ring will be designated by the three ring structure consisting of the furan ring substituents (substituents linked to the 4'- and 5'-carbon atoms), the central benzene ring substituents (substituents linked to the 5- and 8-carbon atoms) and the pyrone ring substituents (substituents linked to the 3- and 4-carbon atoms). More specifically, the present invention contemplates compounds with a primaryamino substituent on the 3- or 4-carbon atom herein referred to as primaryamino-pyrone-linked psoralens and compounds with a primaryamino substituent on the 5- or 8-carbon atom herein referred to as primaryamino -benzene-linked psoralens. In addition, the other of the 3- or 4-carbon atom of a primaryamino -pyrone-linked psoralen may contain an alkyl substituent. Similarly, the other of the 5- or 8 - carbon atom of a primaryamino-benzene-linked psoralen may contain an alkyl substituent.

8-Methoxypsoralen (known in the literature under various names, e.g., xanthotoxin, methoxsalen, 8-MOP) is a naturally occurringlpsoralen with relatively low photoactivated binding to nucleic acids and low mutagenicity in an Ames assay. 4'-Aminomethyl-4,5',8-trimethylpsoralen (AMT) is one of the most reactive nucleic acid binding psoralen derivatives, providing up to 1 AMT adduct per 3.5 DNA base pairs [S. T. Isaacs, G. Wiesehahn and L. M. Hallick, NCI Monograph 66: 21 (1984)]. However, AMT also exhibits significant levels of mutagenicity. A new group of psoralens was desired which would have the best characteristics of both 8-MOP and AMT: low mutagenicity and high nucleic acid binding affinity, to ensure safe and thorough inactivation of pathogens. One group of psoralens that has been synthesized and studied are primaryamino-furan-linked psoralens which are discussed in detail in U.S. Pat. No. 5,593,823. The compounds of the present invention are primaryamino-pyrone and primaryamino-benzene-linked analogs shown to be very effective at inactivation of R17, suggesting very high nucleic acid binding affinity.

Primaryamino-pyrone-linked psoralens are defined as psoralen compounds which have an —NH$_2$ group linked to the 3-or 4-carbon atom of the psoralen by a hydrocarbon chain having a total length of 1 to 24 carbons, where 0 to 3 of those carbons are independently replaced by NH or O, and each point of replacement is separated from each other point of replacement by at least two carbons, and is separated from the psoralen by at least one carbon.

Primaryamino-pyrone-linked psoralens may have additional substituents on the other of the 3- or 4-carbon atom and on the 5-, 8-, 4'-, and 5'-carbon atoms. Said substituents include but are not limited to —H and —$(CH_2)_vCH_3$, where v is a whole number from 0 to 5. Compound I above gives the structure of primaryamino-pyrone-linked psoralens.

Primaryamino-benzene-linked psoralens are defined as psoralen compounds which have an —$NH_2$ group linked to the 5- or 8-carbon at6m of the psoralen by a hydrocarbon chain having a total length of 1 to 24 carbons, where 0 to 3 of those carbons are independently replaced by NH or O, and each point of replacement is separated from each other point of replacement by at least two carbons, and is separated from the psoralen by at least one carbon. Primaryamino-benzene-linked psoralens may have additional substituents on the other of the 5- or 8-carbon atom and on the 3-, 4-, 4'-, and 5'-carbon atoms. Said substituents include but are not limited to —H and —$(CH_2)_vCH_3$, where v is a whole number from 0 to 5. When the primaryamino substituent is on the 8-carbon atom, the present invention is limited in that at least one of the 3-, 5-, 4'- or 5'-substituents is —$(CH_2)_vCH_3$. Compound IV above gives the structure of primaryamino-benzene-linked psoralens.

B. Synthesis of the Primaryamino-Pyrone-Linked Psoralens

Scheme 1 shows a method of synthesis of 3-halomethylcoumarins (1) and 4-halomethylcoumarins (4) useful for the preparation of the primaryamino-pyrone-linked compounds of the present invention. The compounds can be prepared from commercially available materials and converted to phthalimidomethyl-coumarins (2 and 5) and on to aminomethyl-pyrone-linked psoralens (3 and 6) by applying previously described methods [McLleod et al. Tetrahedron Lett. (1972) p. 237; Isaacs et al., Biochem. 16: 1058 (1977)] and further detailed in the examples.

Scheme 1

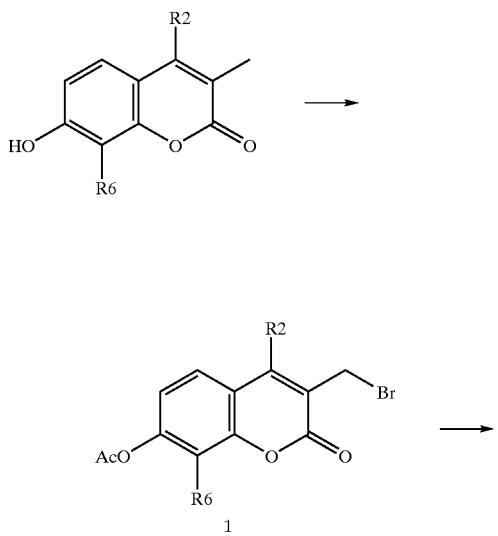

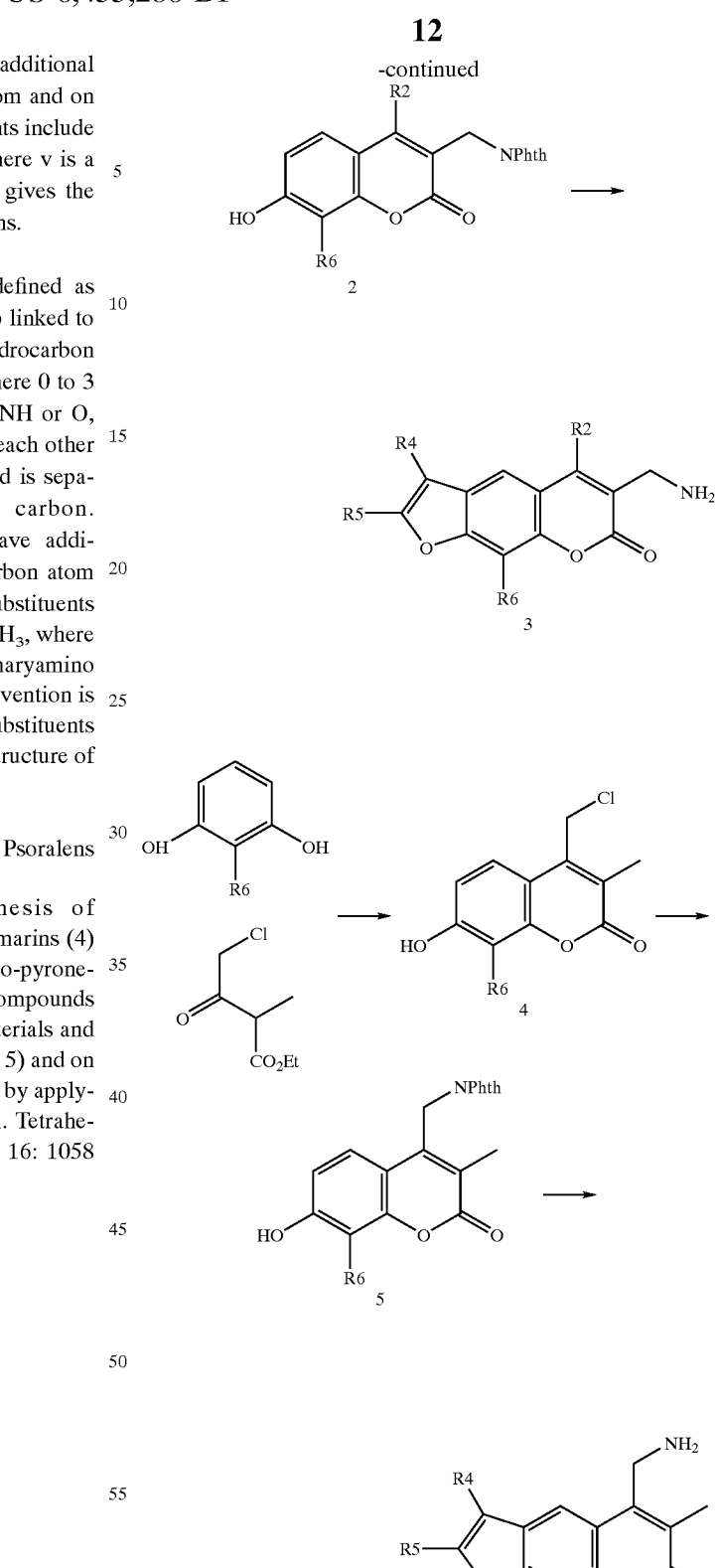

Longer chain aminoalkyl-pyrone linked psoralens can be prepared from the analogous haloalkylcoumarins (7 and 9 as shown in Scheme 2). While there are many ways of making the desired coumarins, many of them can most conveniently be prepared by the Pechman reaction [Organic Reactions, Vol VII, Chap 1, ed. Adams et al., Wiley, N.Y., (1953)] of resorcinols with the functionalized beta-keto esters. The desired beta-keto esters having a halide or halide synthon can be prepared by known methods [e.g., J. March, Advance Organic Chemistry, 3rd Ed., Wiley, (1985) pp437–440 and 824]. For example, Lambert et al., J. Org. Chem., 1985, 50, 5352; Gupta et al., J. Organomet. Chem. 1993, 444,1; Crombie et al., J. Chem. Soc Perk Trans I, 1987,333; Tremul Lozano, Span. Pat. 549788 A1 describe the preparation of desirable beta-keto-esters. The synthesis of such haloalkyl and hydroxyalkylcoumarins have been previously described [Zaniuk et al, Pol. Pat. PL 144435 B1, Fall et al, Heterocycles, (1995) 41, 647].

as shown in the examples. Finally, the use of pseudo halides such as the methanesulfonyl group has been described such as in the reaction of 4'-(4-methanosulfonyloxy-2-oxa)butyl-4,5',8-trimethylpsoralen with sodium azide and subsequently converted into 4'-(4-amino-2-oxa)butyl-4,5',8-trimethylpsoralen. The same synthetic methods can be applied to the 3- and 4-primaryamino substituted psoralens as shown in the examples and typified in scheme 3 for the synthesis of 13 and 16, which have an oxygen atom in the primaryamino substituent chain. The synthesis starts from methoxyalkylcoumarins 7 and 9 above (where Y=OMe) which may be prepared from 7 and 9 (Y=halo, OH) or via direct coumarin synthesis. Conversion to psoralens 11a and 14a follows the same procedures described here in Scheme 1 and elsewhere. The psoralens are then de-methylated in a

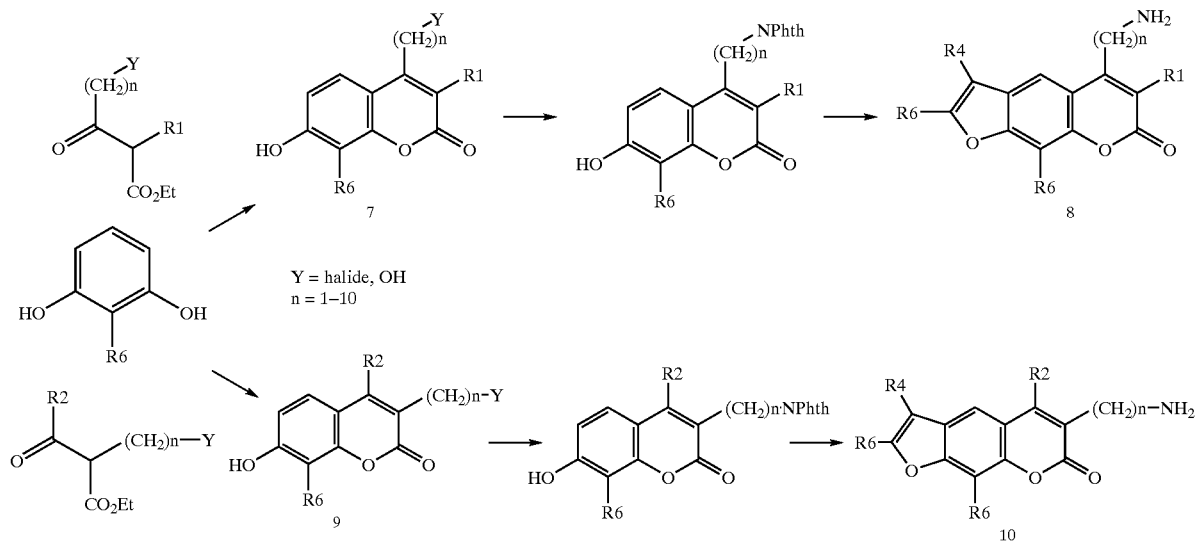

Scheme 2

Alternatively, one can carry the protected alkylcoumarin (e.g. 7 where Y=halo, OH, OMe) through to a haloalkyl-pyrone linked psoralen and prepare the compounds of the present invention by applying some methods known in the art to functionalize haloalkylpsoralens. Examples of such functionalizations include the reaction of 4'-bromomethyl or chloromethylpsoralens (4'-BMT and 4'-CMT respectively) with ammonia, or potassium phthalimide (KPhth) followed by hydrazine to give AMT, as well as the reaction of the 4'-BMT and 4'-CMT with a variety of other amines. The identical reaction of 5'-bromomethyl or chloromethylpsoralen with KPhth is known [Kaufman U.S. Pat. No 4,294,822]. The reaction of 5-chloromethyl8-methoxypsoralen and 8-chloromethyl-5-methoxypsoralen with amines is known.

For the preparation of compounds of the present invention in which the linker between the primary amine and the psoralen contains one or more oxygen, one or more nitrogen, or both oxygen and nitrogen atoms, the preparation of such functionalized systems from haloalkylpsoralens has been thoroughly described previously for 4'- and 5'-primaryamino substituted psoralens [U.S. Pat. No. 5,654,443, incorporated by reference herein]. The same synthetic methods can be applied to the 3- and 4-primaryamino substituted psoralens procedure that provides either the haloalkylpsoralen directly, or a hydroxyalkylpsoralen that is converted to a pseudohaloalkylpsoralen (11b and 14b below). By known procedures, set forth in the examples and elsewhere [U.S. Pat. No. 5,654,443] the haloalkylpsoralens are converted to the primaryamino-pyrone-linked substituted psoralens 13 and 16.

Scheme 3

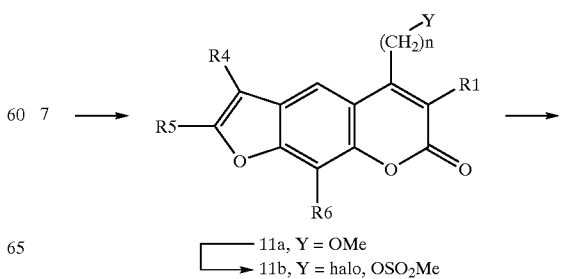

11a, Y = OMe
11b, Y = halo, OSO$_2$Me

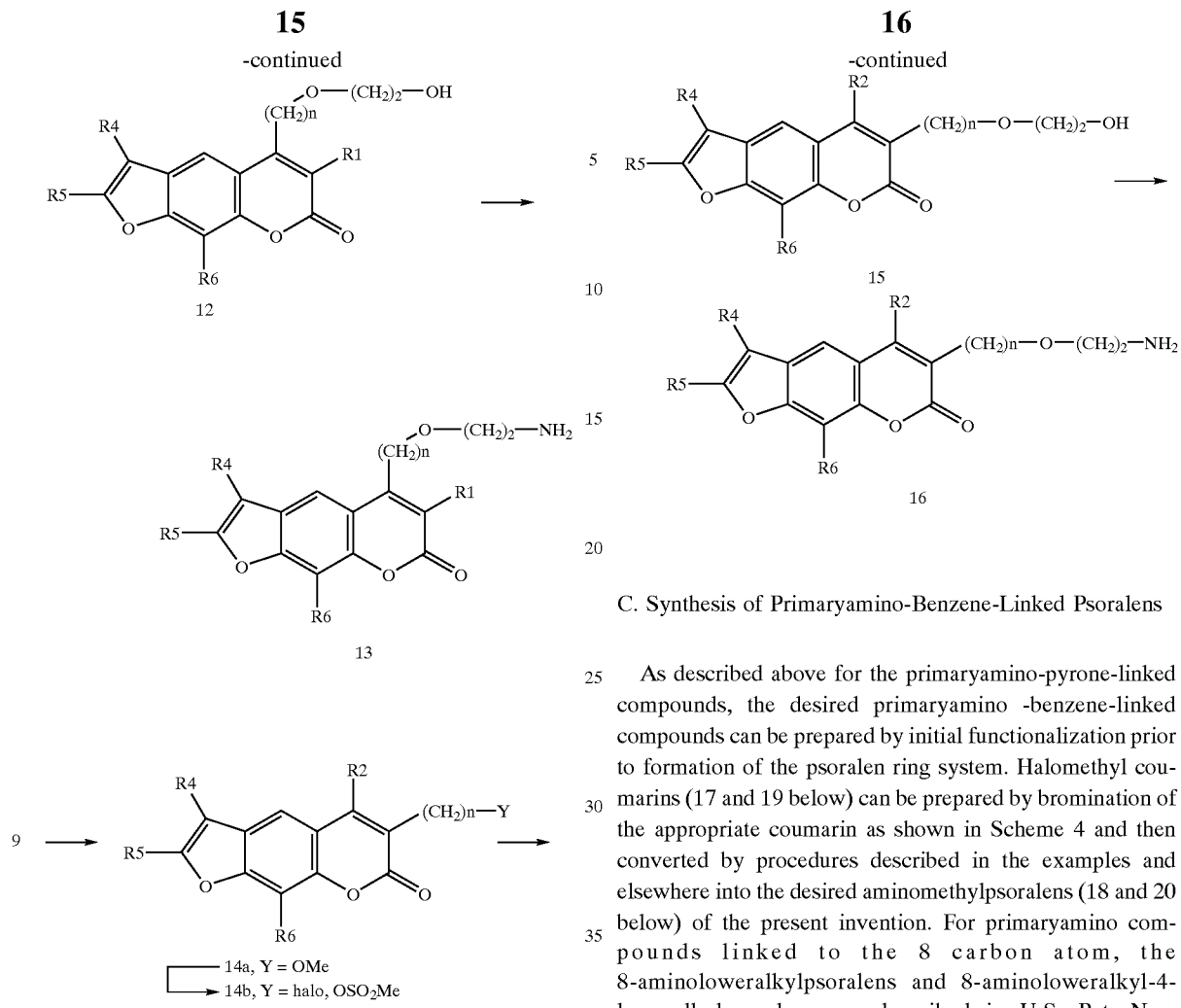

C. Synthesis of Primaryamino-Benzene-Linked Psoralens

As described above for the primaryamino-pyrone-linked compounds, the desired primaryamino -benzene-linked compounds can be prepared by initial functionalization prior to formation of the psoralen ring system. Halomethyl coumarins (17 and 19 below) can be prepared by bromination of the appropriate coumarin as shown in Scheme 4 and then converted by procedures described in the examples and elsewhere into the desired aminomethylpsoralens (18 and 20 below) of the present invention. For primaryamino compounds linked to the 8 carbon atom, the 8-aminoloweralkylpsoralens and 8-aminoloweralkyl-4-loweralkylpsoralens are described in U.S. Pat. Nos. 4,328,239 and 4,269,851, hereby incorporated by reference.

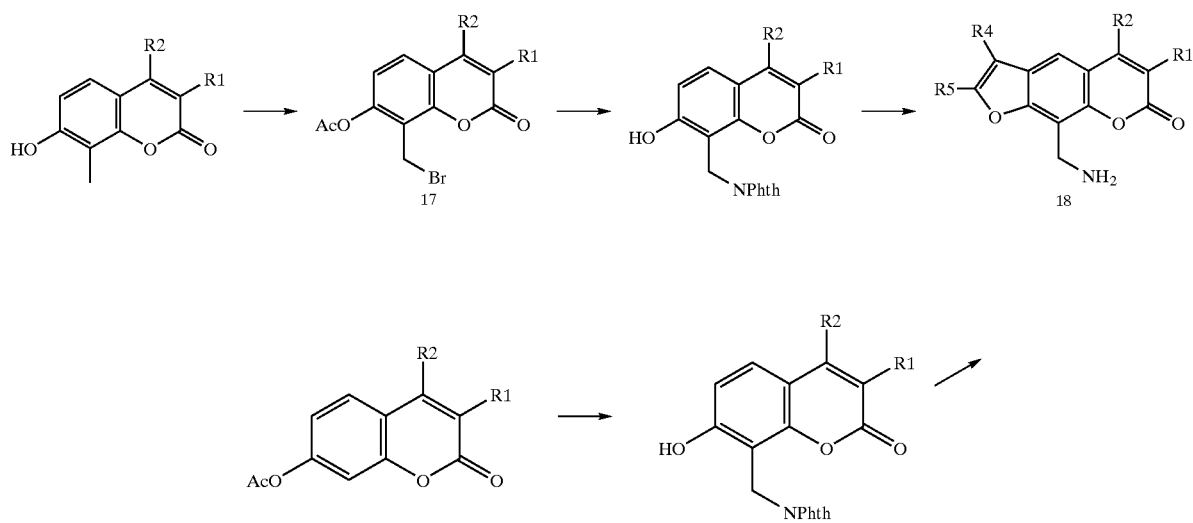

Scheme 4

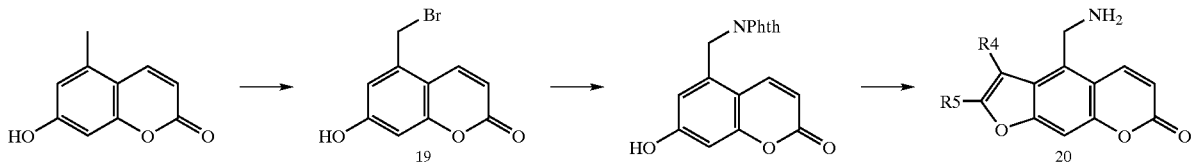

The above aminomethyl-benzene linked compounds and longer chain aminoalkyl-benzene linked psoralens (23 and 26 below) can be prepared by pre forming the analogous haloalkylcoumarins (22 and 25 as shown in Scheme 5). While there are many ways of making the desired coumarins, many of them can most conveniently be prepared by the Pechman reaction [Organic Reactions, Vol VII, Chap 1, ed. Adams et al., Wiley, N.Y., (1953)] of functionalized resorcinols with beta-keto esters. The desired resorcinols having a halide or halide synthon (21 and 24 below) can be prepared by known methods [see for example Makriyannis et al, U.S. Pat. No. 5,440,052; Seebach et al, Helv. Chim. Acta (1994) 77, 1673; Charalambous et al, J. Med. Chem (1992) 35, 3076; Elix et al, Aust. J. Chem. (1987) 40, 1841]. The haloalkylcoumarins can then be converted to protected aminoalkylcoumarins and taken on to the psoralens by methods described in the examples.

functonalize haloalkylpsoralens as shown in Scheme 6 for the synthesis of 28 and 30 below, which have an oxygen atom in the primaryamino substituent chain. The synthesis starts from methoxyalkylcoumarins 22 and 25 above (where Y=OMe) which may be prepared from 22 and 25 (Y=halo, OH) or via direct coumarin synthesis. Conversion to the psoralens, 27 and 29, follows the same procedures described here in Scheme 3 and elsewhere. By known procedures, set forth in the examples, the haloalkylpsoralens are converted to 28 and 30.

For the preparation of primary amino-benzene-linked psoralens in which the linker between the primary amine and the psoralen contains one, or more oxygen, one or more nitrogen, or both oxygen and nitrogen atoms, methods discussed above for the primaryamino-pyrone-linked psoralens can be used.

Scheme 5

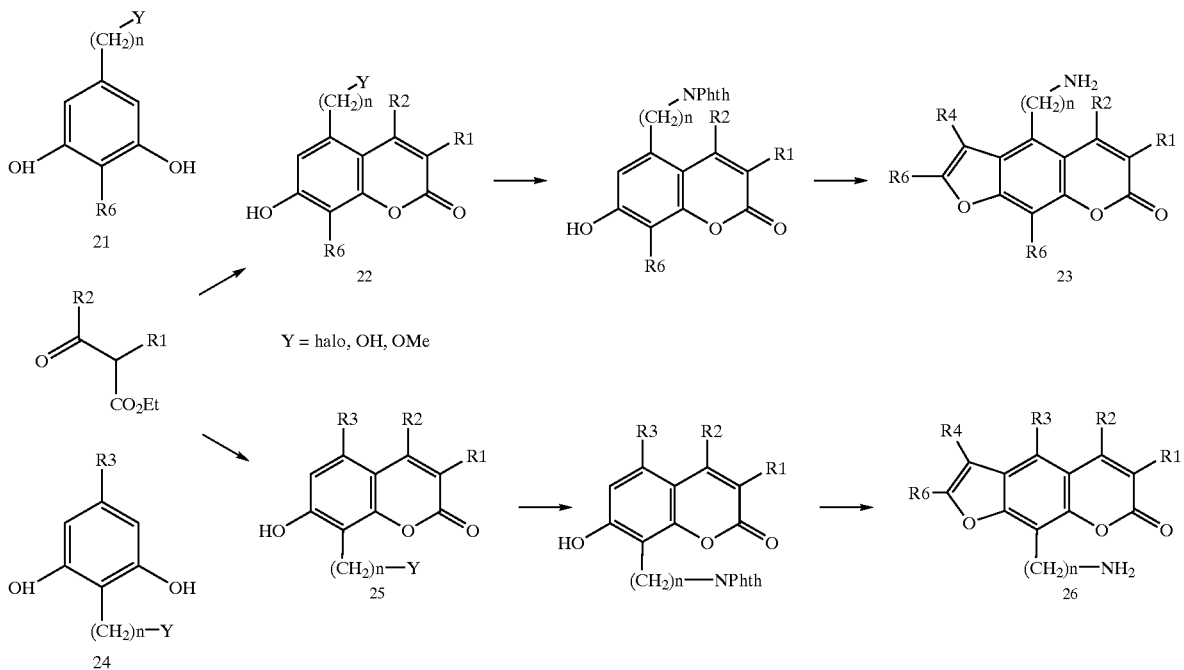

Alternatively, one can carry the protected alkylcoumarin (e.g. 22 and 25 where Y=halo, OH, OMe) through to a haloalkylpyrone-linked psoralen and prepare the compounds of the present invention by methods known in the art to

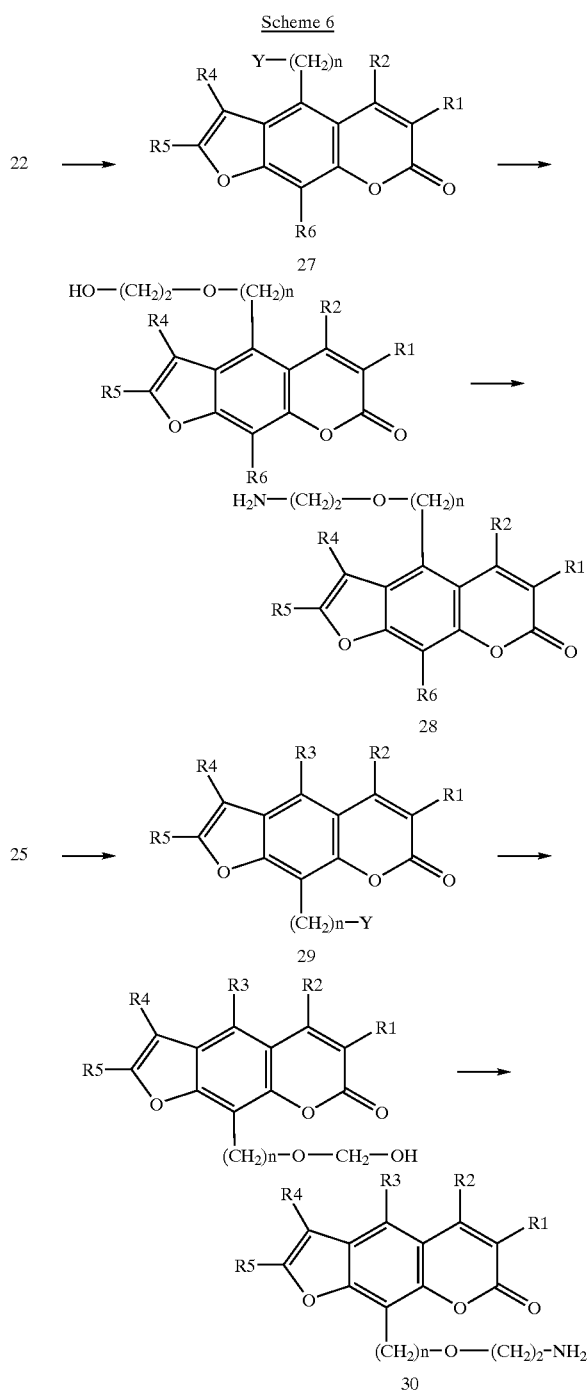

Scheme 6

D. Synthesis of Psoralen Conjugates.

The preparation of psoralen conjugates where the psoralen is linked to nucleotides, biotin, other intercalators, etc. has been described for the 4'-linked psoralens, for the 5-methyl linked-8-methoxypsoralen and for the 8-methyl linked 5-methoxypsoralen. While not being limited to any synthetic method to conjugate the psoralen onto another small molecule, protein, nucleic acid or material surface, typical methods for linking psoralens often entail one of three methods: 1) the bromomethylpsoralen is reacted with an amino or hydroxy function on the conjugated moiety; 2) the aminomethylpsoralen is reacted with an amide, urea or carbamate precursor (e.g., a succinamido group, or an isocyanate) on the conjugating moiety; and 3) the hydroxymethylpsoralen is reacted with an ester, or carbamate precursor on the conjugating moiety.

By the use of such known methods of conjugation, or alternative methods that may provide greater ease of preparation, one can prepare compositions comprising a psoralen linked through the pyrone ring to other nucleic acid binding moieties, to proteins, to nucleic acids, to fluorescent probes or other small molecules useful in diagnostics and to material surfaces.

Likewise, by the use of such known methods of conjugation, or alternative methods that may provide greater ease of preparation, one can prepare compositions comprising a psoralen linked through the benzene ring to other nucleic acid binding moieties, to proteins, to nucleic acids, to fluorescent probes or other small molecules useful in diagnostics and to material surfaces.

II. Photoactivation Devices

A variety of light devices may be useful for the photoactivation of compounds of the present invention and may be useful in the present methodology. Features of possible devices may be found in U.S. Pat. Nos. 5,593,823 and 5,683,661, hereby incorporated by reference. Additional features for possible uses of the compounds of this invention would include a means for passing a solution for inactivation through a light device such that the solution is sufficiently illuminated so as to inactivate pathogens within the solution. Said means may include gravity flow or metered flow, such as through a peristaltic pump or similar flow apparatus.

III. Binding of Compound to Nucleic Acid

The present invention contemplates binding new and known compounds to nucleic acid, including (but not limited to) viral nucleic acid, bacterial nucleic acid, nucleic acid of lymphocytes, and nucleic acid of tissue cells such as smooth muscle cells. One approach of the present invention to binding photoactivation compounds to nucleic acid is photobinding. Photobinding is defined as the binding of photobinding compounds in the presence of photoactivating wavelengths of light. Photobinding compounds are compounds that bind to nucleic acid in the presence of photoactivating wavelengths of light. The present invention contemplates methods of photobinding with compounds of the present invention.

One embodiment of the method of the present invention for photobinding involves the steps: a) providing a photobinding compound of the present invention; and b) mixing the photobinding compound with nucleic acid in the presence of photoactivation wavelengths of electromagnetic radiation.

The invention further contemplates a method for modifying nucleic acid, comprising the steps: a) providing photobinding compound of the present invention and nucleic acid; and b) photobinding the photobinding compound to the nucleic acid, so that a compound:nucleic acid complex is formed.

IV. Inactivation of Nucleic Acid Containing Materials

The present invention contemplates treating a blood product with a photoactivation compound and irradiating to inactivate contaminating pathogen nucleic acid sequences before using the blood product. The present invention could also be applied to inactivation of other nucleic acid containing materials, such as lymphocytes, tissue cells, and solutions containing nucleic acids, for example solutions which have been amplified by polymerase chain reaction or a similar nucleic acid amplification technique.

A. Inactivation In General

The term "inactivation" is here defined as the altering of the nucleic acid in a material so as to render the nucleic acid incapable of replication. When the nucleic acid is that of a pathogen, the inactivation of the nucleic acid renders the pathogen incapable of replication. The inactivation of pathogens is detailed in U.S. Pat. No. 5,593,1823. In addition, inactivation may occur in any cell and the level of inactivation within a cell may be controlled by the level of photobinding of the psoralen to the nucleic acid. The level of photobinding can be controlled by varying either the dose of light used or the dose of the psoralen. The level of inactivation can be controlled, ranging from completely shutting down all cellular functions (high levels of photobinding) to shutting down proliferation of the cell while maintaining cellular functions (low levels of photobinding), i.e. the cell is still capable of transcribing the nucleic acid for the production of proteins. For example, a lymphocyte or tissue cell may be inactivated in that it can not replicate yet can still produce proteins and maintain biological function. This may also be referred to as inhibition of cellular proliferation rather than inactivation.

B. Inactivation of Potential Pathogens

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occurring due to contact with the material. It is recognized that in this practical scenario, it is not essential that the methods of the present invention result in "total inactivation". That is to say, "substantial inactivation" will be adequate as long as the viable portion is insufficient to cause disease. The inactivation method of the present invention renders nucleic acid in pathogens substantially inactivated. In one embodiment, the inactivation method renders pathogen nucleic acid in blood preparations substantially inactivated.

Without intending to be limited to any method by which the compounds of the present invention inactivate pathogens, it is believed that inactivation results from light induced binding of psoralens to pathogen nucleic acid. Further, while it is not intended that the inactivation method of the present invention be limited by the nature of the nucleic acid; it is contemplated that the inactivation method render all forms of nucleic acid (whether DNA, mRNA, etc.) substantially inactivated.

In the case of photoactivation compounds; modifying nucleic acid, it is preferred that interaction of the pathogen nucleic acid (whether DNA, mRNA, etc.) with the photoactivation compound causes the pathogen to be unable to replicate, such that, should a human be exposed to the treated pathogen, infection will not result.

"Synthetic media" is herein defined as an aqueous synthetic blood or blood product storage media. In one embodiment, the present invention contemplates inactivating blood products in synthetic media. This method may reduce product degradation during storage and permits the use of lower concentrations of photoactivation compounds.

The psoralen photoinactivation method inactivates nucleic acid based pathogens present in blood through a single procedure. Thus, it has the potential to eliminate bacteria, protozoa, and viruses as well. Had an effective decontamination method been available prior to the advent of the AIDS pandemic, no transfusion associated HIV transmission would have occurred. Psoralen-based decontamination has the potential to eliminate all infectious agents from the blood supply, regardless of the pathogen involved. Additionally, psoralen-based decontamination has the ability to sterilize blood products after collection and processing, which in the case of platelet concentrates could solve the problem of low level bacterial contamination and result in extended storage life. [J. Morrow et al., JAMA 266: 555–558 (1991); F. Bertolini et al., Transfusion 32: 152–156 (1992)].

A list of viruses which have been photochemically inactivated by one or more psoralen derivatives appears in Table 2 [From Table 1 of Hanson, C. V., Blood Cells 18:7 (1992)]. This list is not exhaustive, and is merely representative of the great variety of pathogens psoralens can inactivate. The present invention contemplates the inactivation of these and other viruses by the compounds described herein. The compounds of the present invention are particularly well suited for inactivating envelope viruses, such as the HIV virus.

TABLE 2

Viruses Photochemically Inactivated by Psoralens

| Family | Virus |
| --- | --- |
| Adeno | Adenovirus 2 |
|  | Canine hepatitis |
| Arena | Pichinde |
|  | Lassa |
| Bunya | Turlock |
|  | California encephalitis |
| Herpes | Herpes simplex 1 |
|  | herpes simplex 2 |
|  | Cytomegalovirus |
|  | Pseudorabies |
| Orothomyxo | Influenza |
| Papova | SV-40 |
| Paramyxo | Measles |
|  | Mumps |
|  | Parainfluenza 2 and 3 |
| Picorna[1] | Poliovirus 1 and 2 |
|  | Coxsackie A-9 |
|  | Echo 11 |
| Pox | Vaccinia |
|  | Fowl Pox |
| Reo | Reovirus 3 |
|  | Blue tongue |
|  | Colorado tick fever |
| Retro | HIV |
|  | Avian sarcoma |
|  | Murine sarcoma |
|  | Murine leukemia |
| Rhabdo | Vesticular stomatitis virus |
| Toga | Western equine encephalitis |
|  | Dengue 2 |
|  | Dengue 4 |
|  | St. Louis encephalitis |

TABLE 2-continued

Viruses Photochemically Inactivated by Psoralens

| Family | Virus |
| --- | --- |
| Hepadna | hepatitis B |
| Bacteriophage | Lambda |
|  | T2 |
| (Rickettsia) | R. akari (rickettsialpox) |

[1]In the article, it was pointed out that Picornaviruses were photoinactivated only if psoralens were present during virus growth.

C. Selecting Photoactivation Compounds for Inactivation of Pathogens

In order to evaluate a compound to decide if it would be useful in the methods of the present invention, two important properties should be considered: the compound's ability to inactivate pathogens and the compounds effect on the suitability of the treated product for its intended use. A discussion of inactivation of pathogens other than the R17 model discussed below can be found in U.S. Pat. No. 5,593,823. This reference enables the selection criteria for use in pathogen inactivation of blood products for the compounds of the present invention. The screening technique used to evaluate the compounds of the present invention is to perform a bacteriophage screen; an assay which determines nucleic acid binding of test compounds. A screen of this type, an R17 screen, is described in detail in EXAMPLE 13, below.

The R17 bacteriophage screen is believed to be predictive of HIV inactivation efficiency, as well as the efficiency of compounds against many other viruses. It is a small, single stranded RNA phage. Without intending to be limited to any means by which the present invention operates, it is expected that shorter pieces of nucleic acid are harder to inactivate because they require a higher frequency of formation of psoralen adducts than do longer pieces of nucleic acid. Further, single stranded RNA pathogens are more difficult to inactivate because psoralens can neither intercalate between base pairs, as with double-stranded nucleic acids, nor form diadducts which function as interstrand crosslinks. Thus it is expected that when inactivation of R17 is achieved, these same conditions will cause the inactivation of many viruses and bacteria. More specifically, those compounds which exhibit >1 log inactivation of R17 (i.e. >90% kill) at a compound concentration in a test medium of 320 $\mu$M or less are expected to be reasonable candidates for inactivation of pathogens in blood products.

V. Preservation of Biochemical Properties of Material Treated

Psoralens are useful in inactivation procedures because the reaction can be carried out at temperatures compatible with retaining biochemical properties of blood and blood products [Hanson, C. V., Blood Cells 18:7 (1992)]. The inactivation compounds and methods of the present invention are especially useful because they provide a means to inactivate pathogens while potentially retaining the suitability of the product for its intended use. The suitability of plasma may be measured by functionality of its protein components, either in whole plasma or after separation into plasma fractions. The suitability of platelets may be determined by methods and criteria similar to those used for establishing the suitability of storage and handling protocols.

VI. Psoralen Conjugates and Other Uses of Psoralens

Because of their affinity for nucleic acids and ability to covalently bind to nucleic acids, compounds of the present invention could be very useful when conjugated to other molecules. The conjugates may be formed by either chemical or photochemical attachment of the psoralen to another molecule, molecular fragment, or ligand. Materials to which psoralen may be conjugated include, but are not limited to, other nucleic acid binding moieties such as acridines or lexitropsins, proteins such as antibodies or receptor ligands, nucleic acids, small molecules useful in diagnostics such as fluorescent probes and biotin, and material surfaces.

The amino terminated chain of the psoralens of the present invention, or the halogen substituted intermediates indicated in EXAMPLES 6–9, are particularly suited to chemical attachment to other molecules. Such amino terminated compounds could be substituted for AMT in the following examples. In Wang Z. et al., J. Am. Chem. Soc. 117(20): 5438–5444 (1995), AMT is conjugated to a protected amino acid and subsequently used to prepare a psoralen:peptide conjugate. Such conjugates could be used to probe sequence specific protein—nucleic acid interactions, or perhaps to selectively control gene expression. Similarly, psoralen may be conjugated to a nucleic acid oligonucleotide which is directed to a specific nucleic acid sequence (Vaghefi et al., PCT publication WO 92/02641). Such conjugates could be used as a control of gene expression or as a site specific probe of the nucleic acid sequence. The conjugation of the psoralen allows for a covalent photochemical attachment of the oligonucleotide to the target sequence. Other molecules conjugated to a psoralen starting from an amino terminal chain of the psoralen include, but are not limited to, biotin, fluorescent dyes, insulin, and lexitropsin, the uses of which are discussed in the references [U.S. Pat. Nos. 4,737,454, and 4,599,303, Biochem. and Biophys. Res. Comm. 141(2): 502–509 (1986), Anti-cancer Drug Design 9: 221–237 (1994)].

Any psoralen could potentially be conjugated to a nucleic acid photochemically. Such photochemical conjugates could be used as probes to specific nucleic acid targets. The photochemically conjugated psoralen could be prepared such that when the modified oligonucleotide pairs with the complementary target nucleic acid, the psoralen can crosslink the probe to the target strand with an additional UV light dose. Preparation and uses of such psoralen-oligonucleotide photochemical conjugates are described in U.S. Pat. Nos. 4,737,454, 4,599,303, and 5,532,146. Similarly, any material with which psoralen can interact and photobind could be photochemically conjugated to psoralen. For example, Bioconjugate Chem. 5(5): 463–467 (1994) give a method of photoreacting a psoralen compound with a polystyrene surface such as a microtiter plate. The psoralen can then be conjugated to another molecule such as an oligonucleotide, peptide, or biotin. While this reference uses psoralens containing a secondary amine, the primaryamino compounds of the present invention would also be useful using the conjugation schemes discussed in the references above.

Other possible uses of the compounds of the present invention include the inactivation of viruses for the purpose of preparing a vaccine, the inhibition of leukocytes to control proliferation yet maintain some function as a means of preventing graft vs. host disease in bone marrow transplants, and the inhibition of smooth muscle cells to control proliferation after injury, for example to prevent restenosis after balloon angioplasty. A discussion of the use of psoralens in vaccine preparation can be found in U.S. Pat. No. 5,106,619. A discussion of the use of 8-Methoxypsoralen for prevention of restenosis can be found in U.S. Pat. No. 5,354,774. These references are herein incorporated by reference.

EXPERIMENTAL

The following examples serve to illustrate certain preferred embodiments and aspects of the present invention and are not to be construed as limiting the scope thereof.

In the experimental disclosure which follows, the following abbreviations apply: J (Joules); TLC (Thin Layer Chromatography); NMR (Nuclear Magnetic Resonance; spectra obtained at room temperature on a Varian Gemini 200 MHz Fourier Transform Spectrometer); THF (tetrahydrofuran); DMF (N,N-dimethylformamide); DMEM (Dulbecco's Modified Eagles Medium); FBS (fetal bovine serum); LB (Luria Broth); EDTA (ethelenediaminetetraacetic acid). Starting materials for the synthesis examples are obtained from common suppliers such as Aldrich Chemicals, Milwaukee, Wis.

When isolating compounds of the present invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed as desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

The following examples serve to illustrate certain preferred embodiments and aspects of the present invention and are not to be construed as limiting the scope thereof.

Example 1

Synthesis of 3-aminomethyl-4,4',8-trimethylpsoralen hydrochloride (Compound 31)

Step 1

A solution of 7-hydroxy-3,4,8-trimethylcoumarin (5.19 g, 25.4 mmol) was refluxed in acetic anhydride (10 mL) for 1.5 hours. The solution was slowly poured into ice water (200 mL) and the resulting solid was filtered, then rinsed with water to yield 7-acetoxy-3,4,8-trimethylcoumarin, a beige solid (6.22 g, 99.5%). $^1$H NMR (CDCl$_3$): δ7.47 (d, J=8.6 Hz, 1H), 7.00 (d, J=8.7 Hz, 1H), 2.40 (s, 3H), 2.37 (s, 3H), 2.29 (s, 3H), 2.22 (s, 3H).

Step 2

A mixture of 7-acetoxy-3,4,8-trimethylcoumarin (6.22 g, 25.3 mmol), N-bromosuccinimide (4.61 g, 25.9 mmol) and benzoyl peroxide (390 mg) were refluxed in carbon tetrachloride for 3.5 hours. The mixture was cooled to room temperature and partitioned between CH$_2$Cl$_2$ and water. The organic layer was separated and washed with water several times, then washed with brine. The organic layer was then dried with anhydrous sodium sulfate and evaporated to give crude product (11.8 g) which was recrystallized twice in toluene to give 7-acetoxy-3-bromomethyl-4,8-dimethylcoumarin, a white crystalline solid (4.86 g, 59%). $^1$H NMR (CDCl$_3$): δ7.54 (d; J=8.8 Hz, 1H), 7.05 (d, J=8.8 Hz, 1H), 4.57 (s, 2H), 2.50 (s, 3H), 2.37 (s, 3H), 2.28 (s, 3H).

Step 3

A mixture of 7-acetoxy-3-bromomethyl-4,8-dimethylcoumarin (200 mg, 0.617 mmol) and potassium phthalimide (126 mg, 0.680 mmol) was stirred overnight at room temperature in DMF (3 mL). The slurry was poured into ice water, filtered and washed with a copious amount of water to remove traces of DMF to give 7-acetoxy-4,8-dimethyl-3-phthalimidomethylcoumarin, a creamy white solid after drying (221 mg, 91.7%). $^1$H NMR (CDCl$_3$): δ7.84–7.67 (m, 4H), 7.55 (d, J=8.8 Hz, 1H), 7.02 (d, J=8.8 Hz, 1H), 4.92 (s, 2H), 2.62 (s, 3H), 2.36 (s, 3H), 2.25 (s, 3H).

Step 4

A solution of 7-acetoxy-4,8-dimethyl-3-phthalimidomethylcoumarin (15.9 g, 40.6 mol) was stirred in methanol (2000 mL) while concentrated H$_2$SO$_4$ (75 mL) was added dropwise. The resulting mixture was refluxed for 3 hours, allowed to cool to room temperature, then chilled in an ice water bath. The precipitate was collected in a Buchner funnel and rinsed with ice cold methanol to give 7-hydroxy-4,8-dimethyl-3-phthalimidomethylcoumarin, a white solid (12.1 g, 85.6%). $^1$H NMR (CD$_3$OD): δ7.87–7.78 (m, 4H), 7.55 (d, J=8.7 Hz, 1H), 6.84 (d, J=8.8 Hz, 1H), 2.61 (s, 3H), 2.23 (s, 3H), the methylene peak is presumably obscured by solvent hydroxy peak at 4.88.

Step 5

A slurry of 7-hydroxy-4,8-dimethyl-3-phthalimidomethylcoumarin (4.00 g, 11.5 mmol), potassium carbonate (4.5 g, 36.9 mmol), chloroacetone (1 mL, 11.5 mmol) and acetone (200 mL) were refluxed overnight. After the solution was allowed to cool to room temperature, CH$_2$Cl$_2$ (200 mL) was added and the resulting solid was filtered off. The remaining solution was cold decolorized with charcoal and the solvent evaporated. The resulting solid was stirred with water, vacuum filtered, and washed with water. After air drying, 4,8-dimethyl-7-(2-oxo)propyloxy-3-(phthalimidomethyl)coumarin (4.06 g, 87.1% ) was obtained as an off-white solid. $^1$H NMR (CDCl$_3$): δ7.66–7.83 (m, 4H), 7.48 (d, J=8.8 Hz, 1H), 6.65 (d, J=8.8 Hz, 1H), 4.91 (s, 2H), 4.62 (s, 2H), 2.59 (s, 3H), 2.35 (s, 3H), 2.32 (s, 3H).

Step 6

Compound 4,8-dimethyl-7-(2-oxo)propyloxy-3-(phthalimidomethyl)coumarin (655 mg, 1.62 mmol) was stirred in concentrated NaOH (30 mL) overnight. The brown solution obtained was poured into ice water (150 mL) and acidified with concentrated H$_2$SO$_4$ to pH 1. The white solid obtained was allowed to stir for several hours, filtered, and rinsed with water. After drying in a vacuum dessicator with phosphorus pentoxide, 3-(o-carboxybenzamido)methyl-4,4', 8-trimethylpsoralen (68.3 mg, 102%) was obtained as a white solid. $^1$H NMR (DMSO-d$_6$): δ8.54 (m, 1H), 7.41–7.93 (m, 6H), 4:45 (d, J=4.8 Hz, 2H), 2.65 (s, 3H), 2.30 (s, 3H).

Step 7

A slurry of the carboxylic acid 3-(o-carboxybenzamido)methyl-4,4',8-trimethylpsoralen (304 mg, 0.751 mmol) in 6N HCl (50 mL) was refluxed overnight. The reaction mixture was extracted with $CH_2Cl_2$. The aqueous acid layer was made basic with solid $K_2CO_3$ and extracted with $CH_2Cl_2$. The organic layer was dried and evaporated to give 3-aminomethyl-4,4',8-trimethylpsoralen (129 mg, 66.8%) as a yellow solid. $^1H$ NMR ($CDCl_3$): $\delta$7.58 (s, 1H), 7.48 (app. quartet, J=1.3 Hz, 1H), 3.91 (s, 2H), 2.59 (s, 6H), 2.29 (d, J=1.2 Hz, 3H).

$^{13}C$ NMR ($CD_3OD$): 8.35, 8.89, 15.57, 39.47, 109.72, 112.54, 116.35, 117.04, 124.85, 125.78, 143.18, 147.91, 148.80, 155.86, 162.55.

Step 8

The free amine 3-aminomethyl-4,4',8-trimethylpsoralen (129 mg, 0.502 mmol) was dissolved in a minimum amount of warm ethanol and acidified with 1M HCl in ether (0.7 mL). After refluxing for a few minutes to expel ether, the solution was allowed to cool to room temperature and chilled in an ice bath. The solid formed was filtered and rinsed with ice cold ethanol to give 3-aminomethyl-4,4',8-trimethylpsoralen hydrochloride (28.9 mg, 19.7%), a yellow solid.

Example 2

Synthesis of 8-aminomethyl-4,4',5'-trimethylpsoralen (Compound 32)

Step 1

Hydroxymethylphthalimide (1.59 g, 8.98 mmol) was added in portions approximately every 10 minutes to a solution of 7-hydroxy-4-methylcoumarin (1.50 g, 8.55 mmol) dissolved in concentrated $H_2SO_4$ (18 mL). More $H_2SO_4$ (4 mL) was added and the slurry was stirred for 1 hour at room temperature. The clear solution was poured into 50 mL of ice water and stirred until the ice melted. The resulting white precipitate was filtered off, rinsed with water and allowed to air dry. After the crude solid was triturated (2×100 mL) with chloroform to remove soluble impurities, 7-hydroxy-4-methyl-8-phthalimidomethylcoumarin, a white solid, was obtained (1.96 g, 68.5%).

$^1H$ NMR ($CDCl_3$): $\delta$7.70–7.96 (m, 4H), 7.50 (d, J=8.8 Hz, 1H), 6.97 (d, J=8.9 Hz, 1H), 6.17 (s, 1H), 5.13 (s, 2H), 2.38 (s, 3H).

Step 2

In the same manner as step 5 of EXAMPLE 1 above using 3-chloro-2-butanone instead of chloroacetone, 7-hydroxy-4-methyl-8-phthalimidomethylcoumarin was reacted to form 4-methyl-7-(1-methyl-2-oxo)propyloxy-8-(phthalimidomethyl)coumarin, a pale yellow solid. $^1H$ NMR ($CDCl_3$): $\delta$7.64–7.88 (m, 4H), 7.46 (d, J=8.9 Hz, 1H), 6.58 (d, J=9.0 Hz, 1H), 6.19 (s, 1H), 5.21 (s, 2H), 4.67 (q, J=6.9 Hz, 1H), 2.37 (s, 3H), 2.02 (s, 3H), 1.42 (d, J=6.8 Hz, 3H).

Step 3

4-Methyl-7-(1-methyl-2-oxo)propyloxy-8-phthalimidomethylcoumarin (2.99 g, 8.92 mmol) was refluxed in 10% NaOH (135 mL) for 30 min. The olive green solution was allowed to cool to room temperature, chilled in an ice bath and acidified with HCl to pH 1. The precipitate obtained was filtered off, washed with water and dried to give 8-(o-carboxybenzamido)methyl-4,4',5'-trimethylpsoralen, an off-white solild (3.15 g, 87.3%). $^1H$ NMR ($DMSO-d_6$): $\delta$8.73–8.86 (m, 1H), 7.83 (s, 1H), 7.40–7.79 (m, 4H), 6.38 (s, 1H), 4.82 (d, J=4.5 Hz, 2H), 2.45 (s, 3H), 2.23 (s, 3H), 3rd methyl group presumably obscured by DMSO peak.

Step 4

In the same manner as step 7 of EXAMPLE 1, 8-(o-carboxybenzamido)methyl-4,4',5'-trimethylpsoralen was reacted to form 8-aminomethyl-4,4',5'-trimethylpsoralen, a light yellow solid. $^1H$ NMR ($CDCl_3$): $\delta$7.47 (s, 1H), 6.25 (s, 1H), 4.32 (s, 2H), 2.51 (s, 3H), 2.43 (s, 3H), 2.19 (s, 3H).

Step 5

In the same manner as step 8 of EXAMPLE 1, 8-Aminomethyl-4,4',5'-trimethylpsoralen was converted to 8-Aminomethyl-4,4',5'-trimethylpsoralen hydrochloride, an off-white solid. $^1H$ NMR ($DMSO-d_6$): $\delta$8.46 (s, 3H), 7.97 (s, 1H), 6.44 (s, 1H), 4.38 (s, 2H), 2.57 (s, 3H), 2.47 (s, 3H), 2.24 (s, 3H).

$^{13}C$ NMR ($CD_3OD$): 7.96, 12.10, 19.53, 19.61, 33.48, 104.92, 112.18, 113.64, 117.22, 117.66, 129.50, 155.30, 156.62, 162.64.

By the same method but using chloroacetone in step 2, 8-aminomethyl-4,5'-dimethylpsoralen hydrochloride (Compound 33) may be prepared.

Example 3

Synthesis of 3-aminomethyl-4,4',5',8-tetramethylpsoralen (Compound 34)

Step 1

In the same manner as step 5 of EXAMPLE 1 but using 3-chloro-2-butanone in place of chloroacetone, 7-hydroxy-4,8-dimethyl-3-phthalimidomethylcoumarin was reacted to form 4,8-dimethyl-7-(1-methyl-2-oxo)propyloxy-3-phthalimidomethylcoumarin, a yellow solid. $^1H$ NMR ($CDCl_3$): $\delta$7.67–7.83 (m, 4H), 7.45 (d, J=8.8 Hz, 1H), 6.63 (d, J=9.0 Hz, 1H), 4.91 (s, 2H), 4.72 (q, J=6.8 Hz, 1H), 2.5,8 (s, 3H), 2.35 (s, 3H), 2.17 (s, 3H), 1.55 (d, J=6.8 Hz, 3H).

Step 2

In the same manner as step 3 of EXAMPLE 2, 4,8-dimethyl-7-(1-methyl-2-oxo)propyloxy-3-phthalimidomethylcoumarin was reacted to form 3-(o-carboxybenzamido)methyl-4,4',5',8-tetramethylpsoralen, an off-white solid. $^1H$ NMR ($DMSO-d_6$): $\delta$8.53 (t, J=1.2 Hz, 1H), 7.80 (s, 1H), 7.37–7.79 (m, 4H), 4.45 (d, J=4.6 Hz, 2H), 2.64 (s, 3H), 2.44 (s, 3H), 2.22 (s, 3H), 4th methyl group presumably obscured by DMSO peak.

Step 3

In the same manner as step 7 of EXAMPLE 1, 3-(o-carboxybenzamido)methyl-4,4',5',8-tetramethylpsoralen was reacted to form 3-aminomethyl-4,4',5',8-tetramethylpsoralen, a pale yellow solid. $^1H$ NMR ($CDCl_3$): $\delta$7.44 (s, 1H), 3.90 (s, 2H), 2.57 (s, 6H), 2.42 (s, 3H), 2.19 (s, 3H).

Step 4

In the same manner as step 8 of EXAMPLE 1, 3-aminomethyl-4,4',5',8-tetramethylpsoralen was converted to 3-aminomethyl-4,4',5',8-teltramethylpsoralen hydrochloride, a yellow solid. $^1H$ NMR ($DMSO-d_6$): $\delta$8.00–8.22 (m, 3H), 7.90 (s, 1H), 4.09 (s, 2H), 2.67 (s, 3H), 2.45 (s, 3H), 2.23 (s, 3H), 4th methyl group presumably obscured by DMSO peak.

$^{13}C$ NMR (DMSO): 7.82, 8.46, 12.01, 16.18, 35.38, 107.71, 110.38, 113.40, 115.62, 115.79, 126.98, 147.78, 152.83, 153.78, 1,54.06, 160.85.

Example 4

Synthesis of 3-amino ethyl-4,5',8-trimethylpsoralen (Compound 35)

Step 1

A slurry of 7-hydroxy-4,8-dimethyl-3-phthalimidomethylcoumarin (649 mg, 1.86 mmol), potassium carbonate (320 mg, 2.60 mmol), potassium iodide (15 mg, 0.093 mmol), and 2,3-dichloro-1-propene (0.20 mL, 2.23 mmol) in DMF (15 mL) was stirred at 55–65° C. for 8 hours, allowed to cool to room temperature, then chilled in an ice water bath. The solid was filtered off to obtain the first crop of crude product (1.09 g). Half of the solvent was removed from the filtrate and after chilling, a second crop of crystals was obtained (33 mg). The solids were combined, dissolved in $CH_2Cl_2$, and washed with water several times. The organic layer was dried and evaporated to give 7-(beta-chloroalyloxy)-4,8-dimethyl-3-phthalimidomethylcoumarin, a white solid (690 mg, 87%). $^1$H NMR ($CDCl_3$): δ7.66–7.83 (m, 4H), 7.49 (d, J=9.1 Hz, 1H), 6.79 (d, J=8.8 Hz, 1H), 5.56 (s, 1H), 5.47 (s, 1H), 4.91 (s, 2H), 4.67 (s, 2H), 2.59 (s, 3H), 2.32 (s, 3H).

Step 2

7-(beta-chloroallyloxy)-4,8-dimethyl-3-phthalimidomethylcoumarin (487 mg, 1.15 mmol) was refluxed in 1,4-diisopropylbenzene (20 mL) for 17 hours. After cooling to room temperature, the beige precipitate (347 mg) consisting of the intermediate 6-(beta-chloroallyl)-4,8-dimethyl-7-hydroxy-3-phthalimidomethylcoumarin and the decomposition product 4,8-dimethyl-7-hydroxy-3-phthalimidomethylcoumarin and residual solvent were collected and rinsed with hexane.

Concentrated $H_2SO_4$ (2.5 mL) was added dropwise to an ice cold slurry of crude product (296 mg) in 70% $H_2SO_4$ and stirred for 25 minutes. The resulting clear solution was poured into ice water (100 mL). The white precipitate was collected by vacuum filtration, rinsed with water and partitioned between $CH_2Cl_2$ (200 mL) and 10% NaOH (50 mL). The aqueous base layer was washed with $CH_2Cl_2$ (2×50 mL) and the organic layers were combined, washed with water (3×100 mL), dried with brine, then with anhydrous sodium sulfate and evaporated. After trituration with ether to remove residual 1,4-diisopropylbenzene, 3-phthalimidomethyl-4,5',8-trimethylpsoralen, a white solid (114 mg, 27.3%) was obtained with 93% purity. $^1$H NMR ($CDCl_3$): δ7.65–7.86 (m, 4H), 7.60, (s, 1H), 6.41 (s, 1H), 4.96 (s, 2H), 2.68 (s, 3H), 2.55 (s, 3H), 2.49 (s, 3H).

Step 3

The 3-phthalimidomethyl-4,5',8-trimethylpsoralen (29.8 mg, 0.0704 mmol) was stirred in THF (2 mL), then 40% aqueous methylamine was added (1 mL). After 20 minutes, the resulting clear yellow solution was evaporated and partitioned between chloroform and 0.3 N HCl. The aqueous acid layer was made basic with solid $K_2CO_3$ and extracted with $CH_2Cl_2$, which was then dried and evaporated to give 3-aminomethyl-4,5',8-trimethylpsoralen (17 mg, 94%), a light yellow solid. $^1$H NMR ($CDCl_3$): δ7.54 (s, 1H), 6.40 (s, 1H), 3.87 (s, 2H), 2.57 (s, 3H), 2.53 (s, 3H), 2.48 (s, 3H).

$^{13}$C NMR ($CDCl_3$): 8.97, 14.65, 15.55, 39.45, 103.12, 109.18, 113.04, 117.02, 125.92, 148.07, 148.18, 155.45, 157.73, 162.72.

Step 4

In the same manner as step 8 of EXAMPLE 1, 3-aminomethyl-4,5',8-trimethylpsoralen was converted to 3-aminomethyl-4,5',8-trimethylpsoralen hydrochloride, a yellow solid. $^1$H NMR ($CD_3OD$): δ7.90 (s, 1H), 6.61 (s, 1H), 4.22 (s, 2H), 2.68 (s, 3H), 2.58 (s, 3), 2.51 (s, 3H).

Example 5

Synthesis of 4-aminomethyl-4',5',8-trimethylpsoralen (Compound 36)

Step 1

In the same manner as step 3 of EXAMPLE 1, 7-acetoxy-4-chloromethyl-8-methylcoumarin (prepared from 7-hydroxy-4-chloromethyl-8-methylcoumarin (obtained as per Zagotto et al., Photochem. Photobio. 58: 486 (1993)) similarly to step 1 of EXAMPLE 1) is reacted to form 7-acetoxy-4-phthalimidomethyl-8-methylcoumarin, a beige solid, was obtained. $^1$H NMR ($CDCl_3$): δ7.76–7.99 (m, 4H), 7.67 (d, J=8.5 Hz, 1H), 7.08 (d, J=8.8 Hz, 1H), 6.23 (s, 1H), 5.00 (s, 2H), 2.38 (s, 3H), 2.29 (s, 3H).

Step 2

In the same manner as step 4 of EXAMPLE 1, 7-acetoxy-4-phthalimidomethyl-8-methylcoumarin was reacted to form 7-hydroxy-4-phthalimidomethyl-8-methylcoumarin, a pale yellow solid. $^1$H NMR (DMSO-$d_6$): δ10.58 (s, 1H), 7.87–8.06 (m, 4H), 7.66 (d, J=8.7 Hz, 1H), 6.93 (d, J=8.8 Hz, 1H), 6.08 (s, 1H), 4.97 (s, 2H), 2.19 (s, 3).

Step 3

In the same manner as step 5 of EXAMPLE 1, using 3-chloro-2-butanone instead of chloroacetone, 7-hydroxy-4-phthalimidomethyl-8-methylcoumarin was reacted to form 8-methyl-7-(1-methyl-2-oxo)propyloxy-4-phthalimidomethylcoumarin a white solid. $^1$H NMR ($CDCl_3$): δ7.73–7.97 (m, 4H), 7.56 (d, J=8.8 Hz, 1H), 6.68 (d, J=8.8 Hz, 1H), 6.09 (s, 1H), 4.96 (s, 2H), 4.75 (q, J=6.9 Hz, 1H), 2.38 (s, 3H), 2.19 (s, 3H), 1.59 (s, 3H).

Step 4

A solution of 8-methyl-7-(1-methyl-2-oxo)propyloxy-4-phthalimidomethylcoumarin (500 mg, 1.23 mmol), 10% NaOH (1.09 mL, 2.46 mmol) and water (25 mL) was heated at 50–60° C. for 4 hours. The slurry was dissolved in water (200 mL) and washed with chloroform. The aqueous acid layer was acidified with 6 N HCl, chilled and filtered to give 4-(o-carboxybenzamido)methyl-4',5',8-trimethylpsoralen, a crude yellow precipitate (470 mg, 93.9% yield of >90% purity). $^1$H NMR (DMSO-$d_6$): δ9.02 (apparent t, J=4.7 Hz, 1H), 7.45–7.98 (m, 5H), 6.56 (s, 1H), 4.78 (s, 2H), 2.45 (s, 3H), 2.22 (s, 3H), third methyl group obscured by DMSO peak.

Step 5

A mixture of 4-(o-carboxybenzamido)methyl-4',5',8-trimethylpsoralen (251 mg, 0.620 mmol), 6 N HCl (30 mL) and water (20 mL) were refluxed for several hours, cooled to room temperature and filtered. The precipitate obtained was a mixture (88 mg) of 4-phthalamidomethyl-4',5',8-trimethylpsoralen and 4-aminomethyl-4',5',8-trimethylpsoralen hydrochloride. A second precipitate formed in the mother liquor and was collected to give 4-aminomethyl-4',5',8-trimethylpsoralen hydrochloride, a yellow solid (41 mg). $^1$H NMR (DMSO-$d_6$): δ8.73 (broad s, 3H), 7.82 (s, 1H), 6.52 (s, 1H), 4.50 (s, 2H), 2.52 (s, 3H), 2.45 (s, 3H), 2.22 (s, 3H).

Example 6

Synthesis of 3-(4-amino-2-oxa)butyl-4,4',8-trimethylpsoralen (Compound 37)

Step 1

7-acetoxy-3-bromomethyl-4,8-dimethylcoumarin (2.50 g, 8.90 mmol) was refluxed in methanol (300 mL) overnight, cooled to room temperature and concentrated under vacuum to give crude 4,8-dimethyl-7-hydroxy-3-methoxymethylcoumarin. $^1$H NMR (CD$_3$OD): δ7.52 (d, J=8.8 Hz, 1H), 6.83 (d, J=8.8 Hz, 1H), 4.50 (s, 2H), 3.41 (s, 3H), 2.49 (s, 3H), 2.25 (s, 3H).

Step 2

In the same manner as step 5 of EXAMPLE 1, 4,8-dimethyl-7-hydroxy-3-methoxymethylcoumarin was reacted to form 4,8-dimethyl-3-methoxymethyl-7-(2-oxo)propyloxycoumarin, a light yellow solid. $^1$H NMR (CDCl$_3$): δ7.47 (d, J=8.9 Hz, 1H), 6.66 (d, J=8.9 Hz, 1H), 4.63 (s, 2H), 4.53 (s, 2H), 3.43 (s, 3H), 2.48 (s, 3H), 2.39 (s, 3H), 2.34 (s, 3H).

Step 3

Crude 4,8-dimethyl-3-methoxymethyl-7-(2-oxo)propyloxycoumarin was refluxed with water (200 mL) and 10% NaOH (3.5 mL) overnight. The basic slurry was chilled, acidified with a few drops of concentrated HCl to pH 1, filtered and rinsed with water. The crude light brown solid was purified by preparative TLC on silica gel with 1% acetonitrile in CH$_2$Cl$_2$ to give 3-methoxymethyl-4,4',8-trimethylpsoralen, a light yellow solid (172.1 mg, 6% yield from 7-acetoxy-3-bromomethyl-4,8-dimethylcoumarin). $^1$H NMR (CDCl$_3$): δ7.60 (s, 1H), 7.47 (s, 1H), 4.58 (s, 2H), 3.45 (s, 3H), 2.61 (s, 3H), 2.58 (s, 3H), 2.28 (s, 3H).

Step 4

Sodium iodide (275 mg, 1.84 mmol) was added to a slurry of 3-methoxymethyl-4,4',8-trimethylpsoralen (250 mg, 0.919 mmol) in acetonitrile. Under nitrogen, trimethylsilyl chloride (0.23 mL, 1.84 mmol) was added and the solution was refluxed for 3 hours. The reaction solvent was evaporated and the reaction partitioned between CH$_2$Cl$_2$ and aqueous sodium thiosulfate. The organic layer was dried with brine, then with anhydrous sodium sulfate and the solvent was removed under vacuum to give 3-iodomethyl-4,4',8-trimethylpsoralen (283 mg, 83.7% crude yield, >90% purity), a beige solid. $^1$H NMR (CDCl$_3$): δ7.61 (s, 1H), 7.49 (s, 1H), 4.54 (s, 2H), 2.59 (s, 3H), 2.48 (s, 3H), 2.29 (s, 3H).

Step 5

A solution of crude 3-iodomethyl-4,4',8-trimethylpsoralen (843 mg) was refluxed with ethylene glycol (35 mL, 650 mmol) in acetone (90 mL) overnight. After the solvent was evaporated, the viscous liquid was partitioned between CH$_2$Cl$_2$ and water to remove excess diol. After several washings with water, the organic layer was dried and evaporated. The crude product was purified on two silica gel preparative TLC plate first eluted with CH$_2$Cl$_2$, then eluted with 2% 2-propanol in CH$_2$Cl$_2$, to give 3-(4-hydroxy-2-oxa)butyl-4,4',8-trimethylpsoralen, a yellow solid (224 mg). $^1$H NMR (CDCl$_3$): δ7.60 (s, 1H), 7.47 (s, 1H), 4.69 (s, 2H), 3.68–3.90 (m, 4H), 2.63 (s, 3H), 2.57 (s, 3H), 2.29 (s, 3H).

Step 6

A mixture of 3-(4-hydroxy-2-oxa)butyl-4,4',8-trimethylpsoralen (214 mg, 0.709 mmol), TEA (0.37 mL, 2.65 mmol), and methanesulfonyl chloride (0.150 mL, 1.94 mmol) in CH$_2$Cl$_2$ (5 mL) was stirred overnight under nitrogen. The reaction mixture was then partitioned between CH$_2$Cl$_2$ and water. The organic layer was washed with water, dried and stripped to give 3-(4-methanesulfonyloxy-2-oxa)butyl-4,4',8-trimethylpsoralen, a yellow solid (220 mg, >90% purity). $^1$H NMR (CDCl$_3$): δ7.63 (s, 1H), 7.49 (app q, J=1.2 Hz, 1H), 4.71 (s, 2H), 4.3–4.47 (m, 2H), 3.79–3.94 (m, 2H), 3.05 (s, 3H), 2.64 (s, 3H), 2.59 (s, 3H), 2.30 (d, J=1.2 Hz, 3H).

Step 7

A mixture of crude 3-(4-methanesulfonyloxy-2-oxa)butyl-4,4',8-trimethylpsoralen (220 mg) and sodium azide (75.3 mg) in ethanol (10 mL) and water (1 mL) was refluxed overnight, evaporated, and azeotroped with toluene. The residue was triturated with CH$_2$Cl$_2$ and filtered to remove insoluble solids. The mother liquor was stripped to give 3-(4-azido-2-oxa)butyl-4,4',8-trimethylpsoralen, a yellow solid (1711 mg, >90% purity). $^1$H NMR (CDCl$_3$): δ7.61 (s, 1H), 7.47 (s, 1H), 4.70 (s, 2H), 3.72–3.82 (m, 2H), 3.35–3.46 (m, 2H), 2.64 (s, 3H), 2.58 (s, 3H), 2.29 (s, 3H). $^{13}$C NMR (CDCl$_3$): 8.32, 8.85, 16.00, 51.27, 65.24, 69.72, 109.66, 112.71, 116.40, 116.80, 119.63, 125.81, 143.29, 149.18, 153.34, 156.26, 162.46.

Step 8

A mixture of crude 3-(4-azido-2-oxa)butyl-4,4',8-trimethylpsoralen (171 mg), triphenylphosphine (205 mg), and water (10 drops) was stirred in THF (9 mL) overnight, evaporated and partitioned between CH$_2$Cl$_2$ and 1M HCl. The aqueous acid layer was made basic with K$_2$CO$_3$ and extracted with CH$_2$Cl$_2$. The organic layer was dried and evaporated to give 3-(4-amino-2-oxa)butyl-4,4',8-trimethylpsoralen, an orange solid (114 mg). $^1$H NMR (CDCl$_3$): δ7.60 (s, 1H), 7.47 (s, 1H), 4.65 (s, 2H), 3.60 (t, J=5.1 Hz, 2H), 2.84–2.97 (m, 2H), 2.62 (s, 3H), 2.57 (s, 3H), 2.28 (s, 3H).

Step 9

Crude 3-(4-amino-2-oxa)butyl-4,4',8-trimethylpsoralen was acidified with 5–6N HCl in isopropanol and evaporated. The salt was recrystallized in isopropanol and the resulting precipitate was washed with hexane to give 3-(4-amino-2-oxa)butyl-4,4',8-trimethylpsoralen hydrochloride, an off white solid (64.5 mg). $^1$H NMR (CD$_3$OD): δ7.89 (s, 1H), 7.67 (app. q, J=1.1 Hz, 1H), 4.70 (s, 2H), 3.74–3.88 (m, 2H), 3.13–3.26 (m, 2H), 2.70 (s, 3H), 2.57 (s, 3H), 2.32 (d, J=1.2 Hz, 3H). $^{13}$C NMR (CD$_3$OD): 8.11, 8.63, 16.22, 40.98, 66.07, 67.60, 110.02, 114.52, 117.59, 117.75, 119.88, 127.20, 145.00, 149.82, 155.43, 157.24, 164.14.

Example 7

4-(4-Amino-2-oxa)butyl-4',5',8-trimethylpsoralen (Compound 38)

Step 1

A mixture of 4-chloromethyl-7-hydroxy-8-methylcoumarin (2.00 g, 8.90 mmol) and sodium methoxide (12.0 g, 222 mmol) in methanol (400 mL) was refluxed overnight. The solution was allowed to cool to room temperature, acidified to pH 0–1 with 5–6N HCl in isopropanol and evaporated. The residue was azeotroped with toluene several times to give crude product 7-hydroxy-4- methoxymethyl-8-methylcoumarin, a yellow oil. $^1$H NMR (CD$_3$OD): δ7.38 (d, J=8.5 Hz, 1H), 6.82 (d, J=8.8 Hz, 1H), 6.29 (s, 1H), 4.66 (s, 2H), 3.51 (s, 3H), 2.26 (s, 3H).

Step 2

In the same manner as step 5 of EXAMPLE 1 but using 3-chloro-2-butanone instead of chloroacetone, 7-hydroxy-4-methoxymethyl-8-methylcoumarin was reacted to form 8-methyl-4-methoxymethyl-7-(1-methyl-2-oxo)propyloxycoumarin, an off-white solid. $^1$H NMR (CDCl$_3$): δ7.34 (d, J=8.8 Hz, 1H), 6.61 (d, J=8.9 Hz, 1H), 6.40 (s, 1H), 4.72 (q, J=6.8 Hz, 1H), 4.57 (d, J=1.3 Hz, 2H), 3.49 (s,, 3H), 2.39 (s, 3H), 2.19 (s, 3H), 1.56 (d, J=6.8 Hz, 2H).

Step 3

Crude 8-methyl-4-methoxymethyl-7-(1-methyl-2-oxo)propyloxycoumarin was refluxed in water (200 mL) and 10% NaOH (2.8 mL) overnight. The basic slurry was chilled, acidified with a few drops of concentrated HCl to pH 1, filtered and rinsed with water to give 4-methoxymethyl-4',5',8-trimethylpsoralen (1.58 g), an off-white solid. $^1$H NMR (CDCl$_3$): δ7.35 (s, 1H), 6.49 (s, 1H), 4.72 (s, 2H), 3.54 (s, 3H), 2.58 (s, 3H), 2.42 (s, 3H), 2.18 (s, 3H).

$^{13}$C NMR (CDCl$_3$): d 8.38, 8.94, 12.43, 159.48, 71.21, 109.62, 110.07, 110.26, 111.13, 113.67, 127.39, 149.73, 152.61, 152.96, 1,55.00, 162.07.

Step 4

A mixture of 4-methoxymethyl-4',5',8-trimethylpsoralen (500 mg, 1.84 mmol) in methylene chloride (20 mL) was chilled to −78° C. A 1M solution of boron tribromide in methylene chloride (2.6 mL, 2.58 mmol) was then added dropwise. The reaction mixture was allowed to stir overnight under a serum cap, and partitioned between methylene chloride and water. The organic layer was dried with brine, then with anhydrous sodium sulfate and evaporated to give 4-hydroxymethyl-4',5',8-trimethylpsoralen (500 mg, 105%), an olive green solid. $^1$H NMR (CDCl3): δ7.30 (s, 1H), 6.57 (s, 1H), 5.00 (s, 2H), 2.53 (s, 3H), 2.42 (s, 3H), 2.17 (s, 3H).

Step 5

In the same manner as step 6 of EXAMPLE 6,4-hydroxymethyl-4',5',8-trimethylpsoralen was reacted to form 4-methanesulfonyloxymethyl-4',5',8-trimethylpsoralen. $^1$H NMR (CDCl$_3$): δ7.31 (s, 1H), 6.51 (s, 1H), 5.49 (d, J=1.1 Hz, 2H), 3.16 (s, 3H), 2.58 (s, 3H), 2.43 (s, 3H), 2.19 (s, 3H).

Step 6

In the same manner as step 5 of EXAMPLE 6,4-methanesulfonyloxymethyl-4',5',8-trimethylpsoralen was reacted to form 4-(4-hydroxy-2-oxa)butyl-4',5',8-trimethylpsoralen. The product was eluted with 80% ethyl acetate, 20% hexane instead of 2% 2-propanol in CH$_2$Cl$_2$. $^1$H NMR (CDCl$_3$): δ7.32 (s, 1H), 6.52 (s, 1H), 4.83 (s, 2H), 3.72–3.93 (m, 4H), 2.55 (s, 3H), 2.41 (s, 3H), 2.17 (s, 3H).

Step 7

In the same manner as step 7 of EXAMPLE 6,4-(4-hydroxy-2-oxa)butyl-4',5',8-trimethylpsoralen was reacted to form 4-(4-methanesulfonyloxy-2-oxa)butyl-4',5',8-trimethylpsoralen was prepared. This crude mesylate (105 mg, approx. 70% pure) was refluxed 1–2 days with sodium azide (90 mg, 1.38 mmol) in ethanol (5 mL) and water (0.5 mL), then evaporated. The residue was triturated with CH$_2$Cl$_2$ and the insoluble solids were filtered off to give 4-(4-azido-2-oxa)butyl-4',5',8-trimethylpsoralen (71.6 mg). $^1$H NMR (CDCl$_3$): δ7.38 (s, 1H), 6.50 (s, 1H), 4.83 (s, 2H), 3.80 (t, J=4.9, 2H), 3.49 (t, J=4.9, 2H), 2.57 (S, 3H), 2.41 (S, 3H), 2.17 (s, 3H).

Step 8

In the same manner as step 8 of EXAMPLE 6, 4-(4-azido-2-oxa)butyl-4',5,8-trimethylpsoralen was reacted to form 4-(4-amino-2-oxa)butyl-4',5,8-trimethylpsoralen. $^1$H NMR (CDCl3): δ7.34 (s, 1H), 6.52 (s, 1H), 4.80 (s, 2H), 3.64–3.75 (m, 3H), 2.92–3.08 (m, 2H), 2.57 (s, 3H), 2.42 (s, 3H), 2.17 (s, 3H).

Step 9

Crude 4-(4-Amino-2-oxa)butyl-4',5,8-trimethylpsoralen was dissolved in boiling isopropanol and hot filtered through fluted filter paper. The hot mother liquor was acidified with 5–6 N HCl in isopropanol to pH 1 and allowed to cool first to room temperature, then in an ice water bath. The solid product was filtered off, rinsed with ice cold isopropanol, then with hexane to give 4-(4-amino-2-oxa)butyl-4',5,8-trimethylpsoralen hydrochloride. $^1$H NMR (CD$_3$OD): δ7.55 (s, 1H), 6.61 (s, 1H), 5.00 (s, 2H), 3.93 (m, 2H), 2.55 (s, 3H), 2.44 (s, 3H), 2.22 (s, 3H). The CH2NH2 peaks lie under solvent peaks at 3.3 ppm.

Example 8

Synthesis of 5-(4-amino-2-oxa)butyl-4',5'-dimethylpsoralen (Compound 39)

Step 1

In the same manner as step 1 of EXAMPLE 1, 7-hydroxy-5-methylcoumarin was reacted to form 7-acetoxy-5-methylcoumarin. $^1$H NMR (CDCl$_3$): δ7.88 (d, J=9.9 Hz, 1H), 6.96 (s, 1H), 6.89 (s, 1H), 6.40 (d, J=9.8 Hz, 1H), 2.52 (s, 3H), 2.33 (s, 3H).

Step 2

In the same manner as step 2 of EXAMPLE 1, 7-acetoxy-5-methylcoumarin was reacted to form 7-acetoxy-5-bromomethylcoumarin without recrystallizing (75–85% purity). $^1$H NMR (CDCl$_3$): δ8.00 (d, J=9.9 Hz, 1H), 7.11 (s, 1H), 7.09 (s, 1H), 6.51 (d, J=9.9 Hz, 1H), 4.62 (s, 2H), 2.34 (s, 3H).

$^{13}$C NMR (CDCl$_3$): 21.56, 28.44, 111.68, 115.50, 116.78, 120.05, 136.61, 139.29, 153.05, 156.01, 160.25, 168.92.

Step 3

In the same manner as step 1 of EXAMPLE 6, 7-acetoxy-5-bromomethylcoumarin was reacted to form crude 7-hydroxy-5-methoxymethylcoumarin. $^1$H NMR (CD$_3$OD): δ8.10 (d, J=9.5 Hz, 1H), 6.82 (s, 1H), 6.68 (s, 1H), 6.22 (d, J=9.7 Hz, 1H), 4.64 (s, 2H), 3.40 (s, 3H).

Step 4

In the same manner as step 5 of EXAMPLE 1, using 3-chloro-2-butanone instead of chloroacetone, 7-hydroxy-5-methoxymethylcoumarin was reacted to form 5-methoxymethyl-7-(1-methyl-2-oxo)propyloxycoumarin. $^1$H NMR (CDCl$_3$): δ7.92 (d, J=9.8 Hz, 1H), 6.84 (s, 1H), 6.66 (s, 1H), 6.29 (d, J=9.8 Hz, 1H), 4.71 (q, J=6.8 Hz, 1H), 4.60 (s, 2H), 3.41 (s, 3H), 2.20 (s, 3H), 1.54 (d, J=6.9 Hz, 3H).

Step 5

5-Methoxymethyl-4',5'-dimethylpsoralen. Crude 5-methoxymethyl-7-(1-methyl-2-oxo)propyloxycoumarin (12.2 g, approx. 90% purity) was refluxed in water (500 mL) and 10% NaOH (17 mL) for 6 hours. The aqueous solution was partitioned between CH$_2$Cl$_2$ and water. The organic layer was washed with water, dried with brine, then with anhydrous sodium sulfate and evaporated to give 5-methoxymethyl-4',5'-dimethylpsoralen, a beige solid (6.87 g, >95% purity). $^1$H NMR (CDCl$_3$): δ8.17 (d, J=9.9 Hz, 1H), 7.33 (s, 1H), 6.40 (d, J=9.9 Hz, 1H), 4.92 (s, 2H), 3.46 (s, 3H), 2.40 (s, 3H), 2.36 (s, 3H).

Step 6

A mixture of 5-methoxymethyl-4',5'-dimethylpsoralen (6.87 g, 26.6 mmol) in methylene chloride (300 mL) was chilled to −78° C., then a 1M solution of boron tribromide in methylene chloride (37.2 mL, 37.2 mmol) was added dropwise under nitrogen. The reaction mixture was allowed to stir overnight under nitrogen, and partitioned between methylene chloride and water. The organic layer was dried with brine, then with anhydrous sodium sulfate and evaporated to give 5-bromomethyl-4',5'-dimethylpsoralen, (5.89 g, 72.1% yield), a black solid. $^1$H NMR (CDCl$_3$): δ8.11 (d, J=9.9 Hz, 1H), 7.33 (s, 1H), 6.49 (d, J=9.9 Hz, 1H), 5.02 (s, 2H), 2.46 (s, 3H), 2.43 (s, 3H).

Step 7

In the same manner as step 5 of EXAMPLE 6, 5-bromomethyl-4',5'-dimethylpsoralen was reacted to form 5-(4-hydroxy-2-oxa)butyl-4',5'-dimethylpsoralen without chromatographic purification (>80% purity). $^1$H NMR (CDCl$_3$): δ8.17 (d, J=9.9 Hz, 1H), 7.33 (s, 1H), 6.40 (d, J=9.9 Hz, 1H), 5.04 (s, 2H), 3.63–3.85 (m, 4H), 2.41 (s, 3H), 2.36 (s, 3H).

$^{13}$C NMR (CDCl$_3$): 11.17, 12.30, 62.37, 65.16, 72.10, 99.83, 109.97, 114.58, 114.71, 126.75, 127.49, 141.31, 152.31, 154.08, 156.04, 161.47.

Step 8

In the same manner as step 6 of EXAMPLE 6, 5-(4-hydroxy-2-oxa)butyl-4',5'-dimethylpsoralen was reacted to form 5-(4-methanesulfonyloxy-2-oxa)butyl-4',5'-dimethylpsoralen. $^1$H NMR (CDCl$_3$): δ8.18 (d, J=9.9 Hz, 1H), 7.35 (s, 1H), 6.42 (d, J=9.9 Hz, 1H), 5.07 (s, 2H), 4.34–4.43 (m, 2H), 3.81–3.90 (m, 2H), 2.97 (s, 3H), 2.41 (s, 3H), 2.36 (s, 3H).

Step 9

In the same manner as step 7 of EXAMPLE 6, 5-(4-methanesulfonyloxy-2-oxa)butyl-4',5'-dimethylpsoralen was reacted to form 5-(4-azido-2-oxa)butyl-4',5'-dimethylpsoralen, a beige solid. $^1$H NMR (CDCl$_3$): δ8.19 (d, J=9.9 Hz, 1H), 7.34 (s, 1H), 6.41 (d, J=9.9 Hz, 1H), 5.06 (s, 2H), 3.72 (t, J=5.0 Hz, 2H), 3.42 (t, J=4.9 Hz, 2H), 2.41 (s, 3H), 2.37 (s, 3H).

Step 10

In the same manner as step 8 of EXAMPLE 6, 5-(4-azido-2-oxa)butyl4',5'-dimethylpsoralen was reacted to form 5-(4-amino-2-oxa)butyl-4',5'-dimethylpsoralen, a light yellow solid. $^1$H NMR (CDCl$_3$): d 8.18 (d, J=9.9 Hz, 1H), 7.32 (s, 1H), 6.39 (d, J=9.9 Hz, 1H), 5.00 (s, 2H), 3.61 (t, J=5.2 Hz, 2H), 2.90 (t, J=5.2 Hz, 2H), 2.40 (s, 3H), 2.35 (s, 3H).

Step 11

5-(4-amino-2-oxa)butyl-4',5'-dimethylpsoralen (232 mg, 0.956 mmol) was dissolved in hot isopropanol and 5–6 N HCl in isopropanol was added until pH 1 was reached. A solid precipitated out and the slurry was allowed to cool to room temperature, then chilled in an ice bath. The precipitate was filtered off with a Buchner funnel and washed first with ice cold isopropanol then with hexane to give 5-(4-amino-2-oxa)butyl-4',5'-dimethylpsoralen hydrochloride (194 mg, 72.6% yield), a beige solid. $^1$H NMR (CD$_3$OD): δ8.40 (d, J=9.9 Hz, 1H), 7.40 (s, 1H), 6.41 (d, J=9.9 Hz, 1H), 5.16 (s, 2H), 3.80 (t, J=4.9 Hz, 2H), 3.16 (t, J=5.0, 2H), 2.42 (s, 3H), 2.40 (s, 3H).

$^{13}$C NMR: 11.05, 11.90, 41.05, 65.81, 67.27, 100.48, 111.29, 114.85, 116.01, 128.12, 128.81, 143.44, 153.35, 155.47, 157.27, 163.19.

Example 9

Synthesis of 8-(4-amino-2-oxa)butyl-4,4',5'-trimethylpsoralen (Compound 40)

Step 1

In the same manner as step 2 of EXAMPLE 1, 7-acetoxy-4,8-dimethylcoumarin was reacted to form 7-acetoxy-8-bromomethyl-4-methylcoumarin. The crude yellow solid was not recrystallized (75–85% purity). $^1$H NMR (CDCl$_3$): δ7.61 (d, J=8.8 Hz, 1H), 7.15 (d, J=8.8 Hz, 1H), 6.31 (s, 1H), 4.68 (s, 2H), 2.43 (s, 6H).

Step 2

In the same manner as step 2 of EXAMPLE 6, 7-acetoxy-8-bromomethyl-4-methylcoumarin is reacted to form 7-hydroxy-8-methoxymethyl-4-methylcoumarin as a yellow solid (85% purity). $^1$H NMR (CD$_3$OD): δ7.44 (d, J=8.8 Hz 1H), 6.84 (d, J=8.8 Hz, 1H), 6.11 (app. q, J=1.1 Hz, 1H), 5.05 (s, 2H), 3.55 (s, 3H), 2.40 (d, J=1.1 Hz, 3H).

Step 3

In the same manner as step 5 of EXAMPLE 1, using 3-chloro-2-butanone instead of chloroacetone, 7-hydroxy-8-methoxymethyl-4-methylcoumarin was reacted to form 8-methoxymethyl-7-(1-methyl-2-oxo)propyloxy-4-methylcoumarin as a yellow solid (>90% purity). $^1$H NMR (CDCl$_3$): δ7.51 (d, J=8.8 Hz, 1H), 6.73 (d, J=8.8 Hz, 1H), 6.18 (s, 1H), 4.65–4.88 (m, 3H), 3.47 (s, 3H), 2.39(s, 3H), 2.36 (s, 3H), 2.22 (s, 3H), 1.58 (d, J=6.8 Hz, 3H).

Step 4

In the same manner as step 5 of example 8, 8methoxymethyl-7-(1-methyl-2-oxo)propyloxy-4-methylcoumarin was reacted to form 8-methoxymethyl-4,4',5'-trimethylpsoralen as a light yellow solid (>93% purity). $^1$H NMR (CDCl$_3$): δ7.55 (s, 1H), 6.26 (s, 1H), 4.98 (s, 2H), 3.50 (s, 3H), 2.52 (s, 3H), 2.44 (s, 3H), 2.20 (s, 3H).

Step 5

In the same manner as step 6 of EXAMPLE 8, 8-methoxymethyl-4,4',5'-trimethylpsoralen was reacted to form 8-bromomethyl-4,4',5'-trimethylpsoralen as a light yellow solid (>93% purity). $^1$H NMR (CDCl$_3$): δ7.54 (s, 1H), 6.28 (s, 1H), 4.97 (s, 2H), 2.52 (s, 3H), 2.46 (s, 3H), 2.20 (s, 3H).

$^{13}$C NMR (CDCl$_3$): 8.32, 12.50, 19.76, 20.18, 109.57, 110.57, 113.47, 114.35, 116.44, 127.93, 148.95, 153.43, 153.64, 153.96, 161.04.

Step 6

In the same manner as step 5 of EXAMPLE 6, 8-bromomethyl-4,4',5'-trimethylpsoralen was reacted to form 8-(4-hydroxy-2-oxa)butyl-4,4',5'-trimethylpsoralen without chromatographic purification. The crude product (>85% purity) was prepared as a mustard yellow solid. $^1$H NMR (CDCl$_3$): δ7.55 (s, 1H), 6.26 (s, 1H), 5.09 (s, 2H), 3.76 (s, 4H), 2.52 (s, 3H), 2.43 (s, 3H), 2.20 (s, 3H).

Step 7

In the same manner as step 6 of EXAMPLE 6, 8-(4-hydroxy-2-oxa)butyl-4,4',5'-trimethylpsoralen to form 8-(4-methanesulfonyloxy-2-oxa)butyl-4,4',5'- trimethylpsoralen (>85% purity) as a yellow-brown solid. $^1$H NMR (CDCl$_3$): δ7.55 (s, 1H), 6.25 (s, 1H), 5.06 (s, 2H), 4.40 (t, J=4.4 Hz, 2H), 3.87 (t, J=4.4 Hz, 2H), 3.03 (s, 3H), 2.52 (s, 3H), 2.43 (s, 3H), 2.20 (s, 3H).

Step 8

In the same manner as step 7 of EXAMPLE 6, 8-(4-methanesulfonyloxy-2-oxa)butyl-4,4',5'-trimethylpsoralen was reacted to form 8-(4-azido-2-oxa)butyl-4,4',5'-trimethylpsoralen, a beige solid (>85% purity). $^1$H NMR (CDCl$_3$): δ7.55 (s, 1H), 6.26 (s, 1H), 5.08 (s, 2H), 3.81 (t, J=5.1 Hz, 2H), 3.41 (t, J=5.1 Hz, 2H), 2.52 (s, 3H), 2.43 (s, 3H), 2.20 (s, 3H).

Step 9

In the same manner as step 8 of EXAMPLE 6, 8-(4-azido-2-oxa)butyl-4,4',5'-trimethylpsoralen was reacted to form 8-(4-amino-2-oxa)butyl-4,4',5'-trimethylpsoralen, a light yellow solid. $^1$H NMR (CDCl$_3$): δ7.53 (s, 1H), 6.25 (s, 1H), 5.04 (s, 2H), 3.66 (t, J=5.1 Hz, 2H), 2.89 (t, J=5.1 Hz, 2H), 2.51 (s, 3H), 2.43 (s, 3H), 2.19 (s, 3H).

Step 10

In the same manner as step 9 of EXAMPLE 7, 8-(4-amino-2-oxa)butyl-4,4',5'-trimethylpsoralen (784 mg) was reacted to form 8-(4-amino-2-oxa)butyl-4,4',5'-trimethylpsoralen hydrochloride (483 mg, 54.9% yield), an off-white solid. $^1$H NMR (CD$_3$OD): δ7.85 (s, 1H), 6.33 (s, 1H), 5.09 (s, 2H), 3.83 (t, J=5.0 Hz, 2H), 3.16 (t, J=5.0 Hz, 2H), 2.59 (s, 3H), 2.451 (s, 3H), 2.25 (s, 3H).

$^{13}$C NMR (CD$_3$OD): 8.03, 12.14, 19.68, 40.95, 62.58, 67.76, 109.12, 111.74, 113.19, 115.87, 117.22, 129.15, 150.61, 154.70, 155.90, 156.54, 163.30.

Example 10

Synthesis of 3-aminomethyl-4'-methylpsoralen (Compound 41)

Step 1

In the same manner as step 1 of EXAMPLE 1, 7-hydroxy-3-methylcoumarin was reacted to form 7-acetoxy-3-methylcoumarin, a beige solid. $^1$H NMR (CDCl$_3$): δ7.51 (s, 1H), 7.42 (d, J=8.4 Hz, 1H), 6.99–7.14 (m, 2H), 2.34 (s, 3H), 2.22 (d, J=1.2 Hz, 3H).

Step 2

In a similar manner as step 2 of EXAMPLE 1, 7-acetoxy-3-methylcoumarin was reacted to form 7-acetoxy-3-bromomethylcoumarin (70% purity), a beige solid. $^1$H NMR (CDCl$_3$): δ7.84 (s, 1H), 7.51 (d, J=8.3 Hz, 1H), 7.03–7.20 (m, 2H), 4.42 (s, 2H), 2.34 (s, 3H).

Step 3

7-acetoxy-3-bromomethylcoumarin (630 mg) was stirred overnight with potassium phthalimide (432 mg, 2.33 mmol) in DMF (100 mL). The reaction solvent was evaporated and the reaction partitioned between CH$_2$Cl$_2$ and water, then washed several times with water, then with aqueous NaHCO$_3$. The organic layer was dried with brine, then with anhydrous sodium sulfate and evaporated. The crude product was recrystallized in acetic acid to give 7-acetoxy-3-phthalimidomethylcoumarin (375 mg, >95% purity), an off-white solid. $^1$H NMR (CDCl$_3$): δ7.73–7.97 (m, 4H), 7.53 (s, 1H), 7.43 (d, J=8.4 Hz, 1H), 7.13 (s, 1H), 7.03 (dd, J=7.5, 2.1, 1H), 4.82 (s, 2H), 2.33 (s, 3H).

Step 4

In a similar manner as step 4 of EXAMPLE 1, 7-acetoxy-3-phthalimidomethylcoumarin was reacted to form 7-hydroxy-3-phthalimidomethylcoumarin, a beige solid. $^1$H NMR (DMSO-d$_6$): δ7.85–7.98 (m, 5H), 7.51 (d, J=8.3 Hz, 1H), 6.72–6.83 (m, 2H), 4.58 (s, 2H).

Step 5

In a similar manner as step 5 of EXAMPLE 1, 7-hydroxy-3-phthalimidomethylcoumarin was reacted to form 7-(2-oxo)propyloxy-3-phthalimidomethylcoumarin, an off-white solid. $^1$H NMR (DMSO-d$_6$): δ7.83–8.04 (m, 5H), 7.60 (d, J=8.8 Hz, 1H), 7.05 (s, 1H), 6.95 (d, J=8.8 Hz, 1H), 4.99 (s, 2H), 4.61 (s, 2H), 2.18 (s, 3H).

Step 6

In a similar manner as step 3 of EXAMPLE 2, 7-(2-oxo)propyloxy-3-phthalimidomethylcoumarin was reacted to form 3-(o-carboxybenzamido)methyl-4'-methylpsoralen, a beige solid. $^1$H NMR (DMSO-d$_6$): δ8.89 (m, 1H), 8.15 (s, 1H), 7.45–8.04 (m, 7H), 4.28 (d, J=5.3 Hz, 2H), 2.29 (s, 3H).

Step 7

In a similar manner as step 7 of EXAMPLE 1, 3-(o-carboxybenzamido)methyl-4'-methylpsoralen, was reacted to form 3-aminomethyl-4'-methylpsoralen, a light yellow solid. $^1$H NMR (CDCl$_3$): δ7.80 (s, 1H), 7.57 (s, 1H), 7.47 (app. q, J=1.3 Hz, 1H), 7.42 (s, 1H), 3.81 (s, 2H), 2.28 (d, J=1.3 Hz, 3H).

Step 8

3-aminomethyl-4'-methylpsoralen hydrochloride. In the similar manner as step 8 of EXAMPLE 1, 3-aminomethyl-4'-methylpsoralen was converted to 3-aminomethyl-4'-methylpsoralen hydrochloride, an off-white solid. $^1$H NMR (CD$_3$OD): δ8.27 (s, 1H), 7.92 (s, 1H), 7.69 (app. q, J=1.3 Hz, 1H), 7.54 (s, 1H), 4.10 (s, 2H), 2.31 (d, J=1.4 Hz, 3H).

Example 11

Synthesis of 4-aminomethyl-4'-methylpsoralen (Compound 42)

Step 1

In the same manner as step 1 of EXAMPLE 1, 7-hydroxy-4-methylcoumarin was reacted to form 7-acetoxy-4-methylcoumarin, a white solid. $^1$H NMR (CDCl$_3$): δ7.61 (d, J=8.4 Hz, 1H), 7.03–7.16 (m, 2H), 6.27 (s, 1H), 2.431 (s, 3H), 2.35 (s, 3H).

Step 2

In a similar manner as step 2 of EXAMPLE 1, 7-acetoxy-4-methylcoumarin was reacted to form crude 7-acetoxy-4-bromomethylcoumarin (60% purity), a beige solid.

Step 3

In a similar manner as step 3 of EXAMPLE 10, 7-acetoxy-4-bromomethylcoumarin was reacted to form 7-acetoxy-4-phthalimidomethylcoumarin (>93% purity), a yellow solid. $^1$H NMR (CDCl$_3$): δ7.74–8.00 (m, 5H), 7.10–7.22 (;m, 2H), 6.25 (s, 1H), 5.00 (s, 2H), 2.35 (s, 3H).

Step 4

In a similar manner as step 4 of EXAMPLE 1, 7-acetoxy-4-phthalimidomethylcoumarin was reacted to form 7-hydroxy-4-phthalimidomethylcoumarin, a yellow solid. $^1$H NMR (DMSO-d$_6$): δ7.83–8.05 (m, 4H), 7.80 (d, J=8.8 Hz, 1H), 6.87 (dd, J=8.7, 2.1 Hz, 1H), 6.78 (s, 1H), 6.09 (s, 1H), 4.97 (s, 2H).

Step 5

In a similar manner as step 5 of EXAMPLE 1, 7-hydroxy4-phthalimidomethylcoumarin was reacted to form 7-(2-oxo)propyloxy-4-phthalimidomethylcoumarin, a pale yellow solid. $^1$H NMR (CDCl$_3$): δ7.76–7.98 (m, 4H), 7.73 (d, J=9.1 Hz, 1H), 6.94 (dd, J=8.9, 2.5 Hz, 1H), 6.80 (d, J=2.5 Hz, 1H), 6.12 (s, 1H), 4.98.(s, 2H), 4.65 (s, 2H), 2.31 (s, 3H).

Step 6

In a similar manner as step 4 of EXAMPLE 5, 7-(2-oxo) propyloxy-4-phthalimidomethylcoumarin is reacted to form 4-(o-carboxybenzamido)methyl-4'-methylpsoralen, a beige solid.

Step 7

In a similar manner as step 7 of EXAMPLE 1, 4-(o-carboxybenzamido)methyl-4'-methylpsoralen was reacted to form 4-aminomethyl-4'-methylpsoralen, a light yellow solid. $^1$H NMR (CDCl$_3$): δ7.70 (s, 1H), 7.48 (s, 1H), 7.45 (s, 1H), 6.57 (s, 1H), 4.21 (s, 2H), 2.29 (s, 3H).

Step 8

4-aminomethyl-4'-methylpsoralen hydrochloride. In a similar manner as step 9 of EXAMPLE 6, 4-aminomethyl-4'-methylpsoralen was converted to 4-aminomethyl-4'-methylpsoralen hydrochloride, an off-white solid. $^1$H NMR (CD$_3$OD): δ8.00 (s, 1H), 7.71 (s, 1H), 7.56 (s, 1H),: 6.45 (s, 1H), 4.61 (s, 2H), 2.35 (s, 3H).

Example 12

Synthesis of 5-aminomethylpsoralen (Compound 43)

Step 1

In a similar manner as step 3 of EXAMPLE 1, 5-bromomethylpsoralen is reacted to form 5-phthalimidomethylpsoralen, a white solid. $^1$H NMR (CDCl$_3$): δ8.73 (d, J=10.0 Hz, 1H), 7.67–7.89 (m, 5H), 7.47 (s, 1H), 7.38 (d, J=2.2 Hz, 1H), 6.50 (d, J=9.9 Hz, 1H), 5.27 (s, 2H).

Step 2

A slurry of 5-phthalimidomethylpsoralen (300 mg, 0.879 mmol) and hydrazine acetate (648 mg, 7.03 mmol) in ethanol (15 mL) was refluxed for 2 hours. The black solution was evaporated and the residue was partitioned between methylene chloride and dilute aqueous HCl. The aqueous acid layer was washed with methylene chloride, then made basic with solid K$_2$CO$_3$ and extracted with methylene chloride. The final organic layer was dried and evaporated to give 5-aminomethylpsoralen. $^1$H NMR (CDCl$_3$): δ8.25 (d, J=9.9 Hz, 1H), 7.71 (d, J=2.2 Hz, 1H), 7.42 (s, 1H), 6.95 (d, J=1.4 Hz, 1H), 6.45 (d, J=9.9 Hz, 1H), 4.32(s, 2H).

Step 3

In the similar manner as step 9 of EXAMPLE 6, 5-aminomethylpsoralen was converted to 5-aminomethylpsoralen hydrochloride, an off-white solid. $^1$H NMR (CD$_3$OD): δ(8.40 (d, J=9.9 Hz, 1H), 8.02 (d, J=2.2 Hz, 1H), 7.69 (s, 1H), 7.26 (d, 1.5 Hz, 1H), 6.54 (d, J=10 Hz, 1H), 4.74 (s, 2H).

Example 13

The R17 was grown up in Hfr 3000 bacteria, approximate titer 5×10$^{11}$. (R17 and Hfr 3000 were obtained from American Tissue Culture Collection (ATCC), Washington, D.C.) The R17 phage stock was added to a solution of 15% fetal bovine serum in DMEM to a final phage concentration of 10$^8$/mL. An aliquot (0.5 mL) was transferred to a 1.5 mL snap-top polyethylene tube. An aliquot (0.004–0.040 mL) of the test compound stock solution prepared in water, ethanol or dimethylsulfoxide at 0.5 mM was added to the tube. Compounds were tested at concentrations between 4 μM and 32 μM. (AMT is commercially available from HRI, Inc., Concord, Calif.; 8-MOP is commercially available from Sigma, St. Louis, Mo.). The tubes were placed in a light device similar to that described in U.S. Pat. No. 5,593,823 (Baxter Ultraviolet Irradiation System, modified #4R4440) and irradiated at a dose setting of 1 J/cm$^2$. Sterile 13 mL dilution tubes were prepared; each test compound required one tube with 0.4 mL of LB broth and five tubes containing 0.5 mL of LB broth. To make the dilutions, a 0.100 mL aliquot of the irradiated solution of phage and test compound was added to the first dilution tube of 0.4 mL of media then 0.020 mL of this solution was added to the second tube of 0.5 mL medium (1:25). The second solution was then diluted serially (1:25) into the remaining tubes. To each diluted sample was added 0.050 mL of Hfr 3000 bacteria cultured overnight and 3 mL of molten LB top agar and the mixed materials were poured onto LB broth plates. After the top agar hardened, the plates were incubated at 37° C. overnight. The plaque forming units were then counted the following morning and the titer of the phage remaining after phototreatment was calculated based on the dilution factors.

The following controls were run: the "phage only" in which phage was not treated with test compound and not irradiated (listed as "starting titer" in the tables below); and the "dark" control in which the phage/test compound solution was not irradiated before it was diluted and plated. A "UV only" control in which the phage was illuminated without treatment with test compound was not run with these experiments. This control has been shown to have no significant inactivation of R17 in various other studies (data not shown). The dark control was not run on all compounds tested but no significant inactivation of R17 was observed in the compounds tested. Similar controls have been run on other psoralens, mostly 4' and 5' amino substituted psoralens with no significant inactivation of R17 as well (data not shown).

TABLES 3, below, shows the results of various experiments which tested a number of compounds of the present invention according to the R17 protocol just described. AMT was also run for comparison. The number of replicate experiments done for each compound is indicated. The results indicate that all of the compounds selected are likely to meet the selection criteria of >1 log inactivation at 320 μM. Most of the compounds tested were at least as effective as AMT while 3-(4-amino-2-oxa)butyl4,5',8-trimethylpsoralen was at least twice as effective as AMT (i.e. similar levels of inactivation at a given concentration of AMT were achieved at less than half of the concentration, data not shown). The structure of 3-(4-amino-2-oxa)butyl-4,5',8-trimethylpsoralen is shown below.

TABLE 3

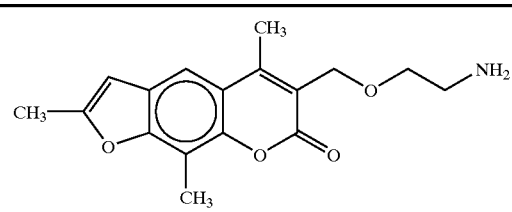

Log inactivation of R17 with compound at 4 μM and 32 μM

| Compound Number (per EXAMPLES 1–12) | Average log Inactivation[a] | | Average Log Titer[b] |
|---|---|---|---|
| | 4 μM | 32 μM | |
| AMT | 1.6 | >6.5 | 7.5 |
| 41 | 0 | 0.6 | 8.0 |
| 31 | 3.1 | N/A | N/A |
| 35 | 1.6 | N/A | N/A |
| 34 | 1.4 | N/A | N/A |
| 37 | 4.3 | >6.5 | 7.5 |
| 42 | 0 | 1.2 | 8.0 |
| 36 | 0.1 | 1.1 | 7.1 |
| 38 | 2.2 | ≧4.0 | 7.5 |
| 39 | 1.6 | >6.6 | 7.6 |
| 33 | 0.4 | 1.7 | 7.1 |
| 32 | 1.1 | N/A | N/A |
| 40 | 2.1 | >6.3 | 7.3 |

[a] Average of 1–4 replicates.
[b] This is the log titer of R17 prior to inactivation.

Example 14

Pathogen inactivation efficiency of three compounds tested in the previous example were evaluated by examining the ability of the compounds to inactivate cell-free virus (HIV). Inactivation of cell-free HIV was performed as follows.

Small aliquots of the compounds were added to stock HIV-1 to a compound concentration of 32 μM in a total of 0.5 mL. The stock HIV ($10^5$–$10^7$ plaque forming units/mL) was in DMEM/15% FBS. The 0.5 mL test aliquots were placed in 24 well polystyrene tissue culture plates and irradiated with 320–400 nm (20 mW/cm$^2$) for 1 minute on a device similar to the device of EXAMPLE 13. Controls included HIV-1 stock only, HIV-1 plus UVA only, and HIV-1 plus the highest concentration of each psoralen tested, with no UVA. Post irradiation, all samples were stored frozen at −70° C. until assayed for infectivity by a microtiter plaque assay. Aliquots for measurement of residual HIV infectivity in the samples were withdrawn and cultured.

Residual HIV infectivity was assayed using an MT-2 infectivity assay. (Previously described in Hanson, C. V., Crowford-Miksza, L. and Sheppard, H. W., J. Clin. Micro 28:2030 (1990)). The assay medium was 85% DMEM (with a high glucose concentration) containing 100 μg of streptomycin, 100 U of penicillin, 50 μg of gentamicin, and 1 μg of amphotericin B per mL, 15% FBS and 2 μg of Polybrene (Sigma Chemical Co., St. Louis, Mo.) per mL. Test and control samples from the inactivation procedure were diluted in a mixture of 50% assay medium and 50% normal human serum. The samples were serially diluted directly in 96-well plates (Corning Glass Works, corning, N.Y.). The samples were mixed on an oscillatory shaker for 30 seconds and incubated at 37° C. in a 5% CO$_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% CO$_2$, 0.075 mL of assay medium containing 1.6% SeaPlaque agarose (FMC Bioproducts, Rockland, Me.) and pre warmed to 38.5° C. was added to each well. The plates were kept at 37° C. for a few minutes until several plates had accumulated and then centrifuged in plate carriers at 600×g for 20 minutes. In the centrifuge, cell monolayers formed prior to gelling of the agarose layer. The plates were incubated for 5 days at 37° C. in 5% CO$_2$ and stained by the addition of 0.05 mL of 50 μg/mL propidium iodide (Sigma Chemical Co.) in phosphate-buffered saline (pH 7.4) to each well. After 24 to 48 hours, the orange fluorescence-stained microplaques were visualized by placing the plates on an 8,000 μW/cm$^2$ 304 nm UV light box (Fotodyne, Inc., New Berlin, Wis.). The plaques were counted at a magnification of ×20 to ×25 through a stereomicroscope. The results are shown in TABLE 4, below.

The results support that the compounds of the present invention are effective in inactivating HIV. In fact, the data for these compounds is comparable to levels of inactivation observed for AMT (data not shown).

TABLE 4

Log kill of cell-free HIV with 1 minute irradiation with compound at 32 μM

| Compound Number | Log Kill | Log Titer |
|---|---|---|
| 31 | 1.9 | 5.3 |
| 34 | 3.5 | 5.5 |
| 32 | 1.1 | 5.4 |

It is to be understood that the invention is not to be limited to the exact details of operation or exact compounds, composition, methods, or procedures shown and described, as modifications and equivalents will be apparent to one skilled in the art.

We claim:

1. A method of treating a biological composition suspected of containing a pathogen, comprising, in the following order:

a) providing, in any order, i) a compound of the formula selected from the group consisting of

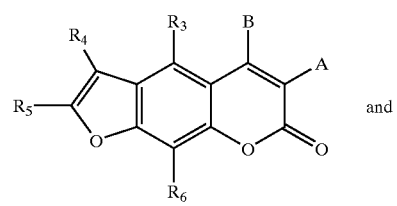

and

-continued

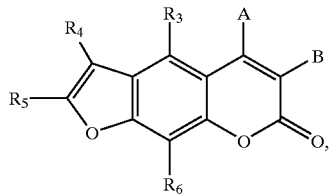

wherein:
I) a substituent A on the pyrone ring is selected from the group consisting of:
—(CH$_2$)$_u$—NH$_2$,
—(CH$_2$)$_w$—J—(CH$_2$)$_z$—NH$_2$,
—(CH$_2$)$_w$—J—(CH$_2$)$_x$—K—(CH$_2$)$_z$—NH$_2$, and
—(CH$_2$)$_w$—J—(CH$_2$)$_x$—K—(CH$_2$)$_y$—L—(CH$_2$)$_z$—NH$_2$;
wherein J, K, and L are independently selected from the group consisting of O and NH, in which u is a whole number from 1 to 10, w is a whole number from 1 to 5, x is a whole number from 2 to 5, y is a whole number from 2 to 5, and z is a whole number from 2 to 6; and
II) substituents B, R$_3$, R$_4$, R$_5$, and R$_6$ on the pyrone ring, 5-, 4'-, 5'- and 8-carbon atoms respectively, are independently selected from the group consisting of —H and —(CH$_2$)$_v$CH$_3$, where v is a whole number from 0 to 5; and all salts thereof; ii) a light source for photoactivating said compound; and iii) a biological composition suspected of containing a pathogen;

b) adding said compound to said biological composition; and c) photoactivating said compound, so as to inactivate said pathogen.

2. The method of claim 1, wherein said biological composition is a blood product.

3. The method of claim 2, wherein said blood product comprises plasma.

4. The method of claim 2, wherein said blood product comprises a plasma fraction.

5. The method of claim 2, wherein said blood product comprises platelets.

6. The method of claim 2, wherein said pathogen is selected from the group consisting of viruses and bacteria.

* * * * *